(12) United States Patent
Chu et al.

(10) Patent No.: US 12,011,206 B2
(45) Date of Patent: Jun. 18, 2024

(54) MEDICAL SYSTEMS, DEVICES, AND RELATED METHODS

(71) Applicant: Boston Scientific Scimed, Inc., Maple Grove, MN (US)

(72) Inventors: Michael S. H. Chu, Brookline, MA (US); Sacha Tang, Lowell, MA (US); Pat S. Phongsavanh, Blackstone, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 173 days.

(21) Appl. No.: 17/453,037

(22) Filed: Nov. 1, 2021

(65) Prior Publication Data

US 2022/0133383 A1    May 5, 2022

Related U.S. Application Data

(60) Provisional application No. 63/108,590, filed on Nov. 2, 2020.

(51) Int. Cl.
*A61B 18/08*    (2006.01)
*A61B 1/00*    (2006.01)
(Continued)

(52) U.S. Cl.
CPC ........ *A61B 18/085* (2013.01); *A61B 1/00066* (2013.01); *A61B 1/00101* (2013.01);
(Continued)

(58) Field of Classification Search
CPC .............. A61B 18/085; A61B 1/00066; A61B 1/00101; A61B 1/0014; A61B 1/018; A61B 17/1227; A61B 17/128; A61B 2017/00296; A61B 2018/00577; A61B 17/29; A61B 18/1445; A61B 18/1492;
(Continued)

(56) References Cited

U.S. PATENT DOCUMENTS 3,739,784 A  *  6/1973  Itoh ........................ A61B 1/018
                                            606/113
5,320,630 A      6/1994  Ahmed
                        (Continued)

FOREIGN PATENT DOCUMENTS

JP      S59 184801       12/1984
WO      WO 2018/229047 A1  12/2018

OTHER PUBLICATIONS

International Search Report and Written Opinion of the International Search Authority dated Feb. 9, 2022, issued in International Application No. PCT/US2021/072147, filed Nov. 1, 2021 (13 pages).

*Primary Examiner* — Katherine H Schwiker
*Assistant Examiner* — Zehra Jaffri
(74) *Attorney, Agent, or Firm* — Bookoff McAndrews, PLLC

(57) ABSTRACT

In one example, a medical device may be adapted for use with a delivery device, and the medical device may include a handle including at least one actuator; a body adapted to releasably mount to a distal portion of the delivery device, the body supporting a pair of jaws rotatably coupled to the body; and a control wire coupled to the pair of jaws and the actuator. The actuator may be configured to open and close the pair of jaws.

15 Claims, 10 Drawing Sheets

(51) Int. Cl.
  *A61B 1/018* (2006.01)
  *A61B 17/00* (2006.01)
  *A61B 17/122* (2006.01)
  *A61B 17/128* (2006.01)
  *A61B 18/00* (2006.01)

(52) U.S. Cl.
  CPC ............ *A61B 1/0014* (2013.01); *A61B 1/018* (2013.01); *A61B 17/1227* (2013.01); *A61B 17/128* (2013.01); *A61B 2017/00296* (2013.01); *A61B 2018/00577* (2013.01)

(58) Field of Classification Search
  CPC ........ A61B 2017/2938; A61B 1/00087; A61B 1/00089; A61B 17/1285; A61B 17/320016; A61B 2017/00269; A61B 2017/00353; A61B 2017/00407; A61B 2017/00867; A61B 2017/00907; A61B 1/0052; A61B 17/12; A61B 2017/12004; A61B 17/12009; A61B 17/12013; A61B 2017/12018; A61B 2017/320095
  See application file for complete search history.

(56) References Cited

U.S. PATENT DOCUMENTS

| | | |
|---|---|---|
| 6,849,078 B2 | 2/2005 | Durgin et al. |
| 2002/0133178 A1* | 9/2002 | Muramatsu ........ A61B 17/1285 606/142 |
| 2002/0173786 A1* | 11/2002 | Kortenbach ........... A61B 10/06 606/49 |
| 2004/0006256 A1* | 1/2004 | Suzuki ............... A61B 1/00133 600/140 |
| 2006/0252993 A1* | 11/2006 | Freed ................... A61B 1/0052 604/95.04 |
| 2007/0244512 A1* | 10/2007 | Measamer ............ A61B 10/06 606/205 |
| 2009/0306658 A1* | 12/2009 | Nobis ................. A61B 18/1482 606/46 |
| 2010/0010511 A1 | 1/2010 | Harris et al. |
| 2012/0239061 A1* | 9/2012 | Mathur ............. A61B 17/12013 606/140 |
| 2013/0144312 A1 | 6/2013 | Schostek et al. |
| 2013/0225934 A1 | 8/2013 | Raybin et al. |
| 2014/0213847 A1* | 7/2014 | Green ............. A61B 17/00234 600/104 |
| 2014/0228864 A1* | 8/2014 | Jugenheimer ........ A61B 17/122 606/157 |
| 2016/0038133 A1 | 2/2016 | Smith et al. |

\* cited by examiner

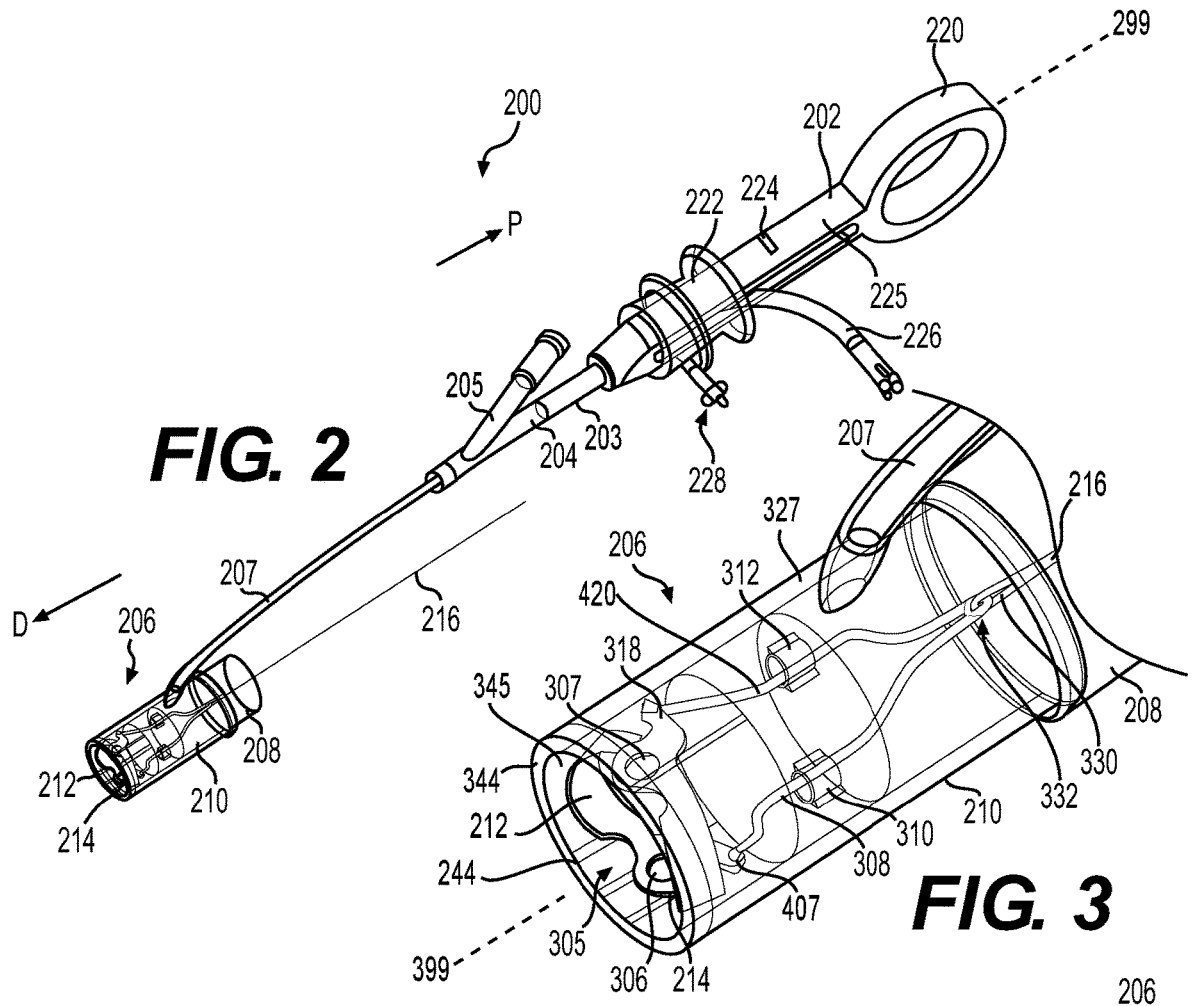
FIG. 2
FIG. 3
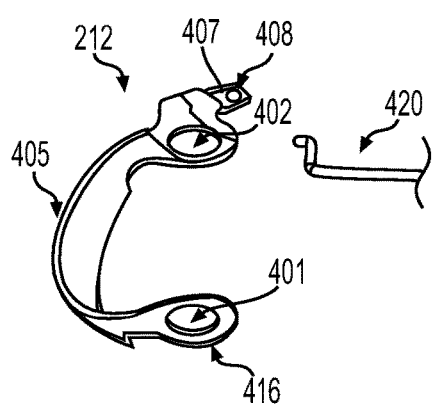
FIG. 4
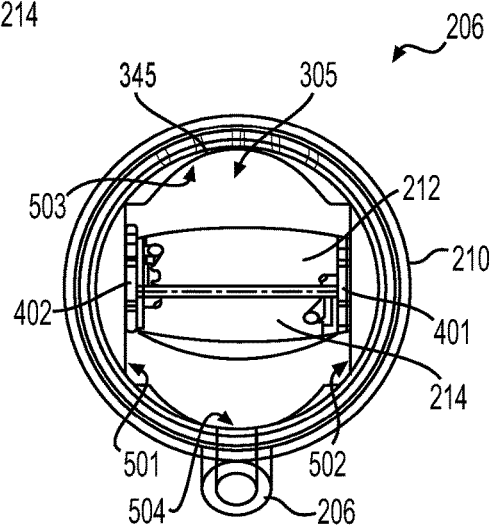
FIG. 5

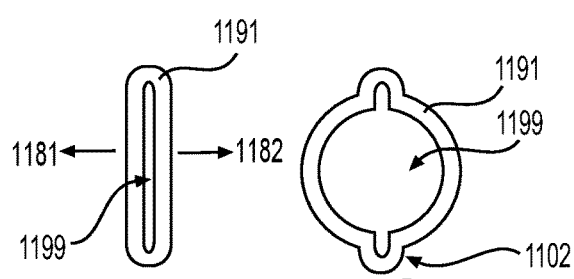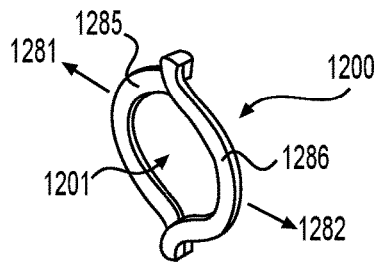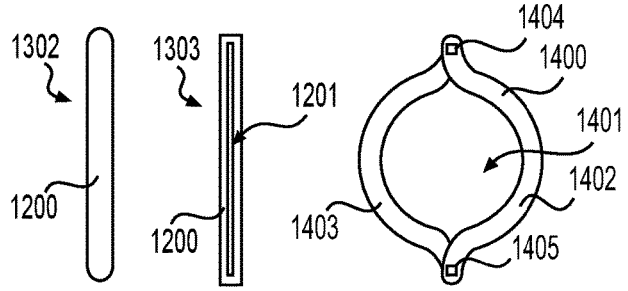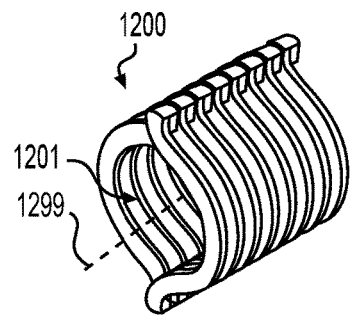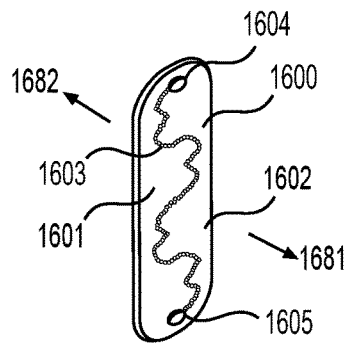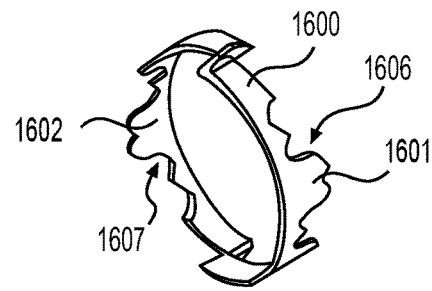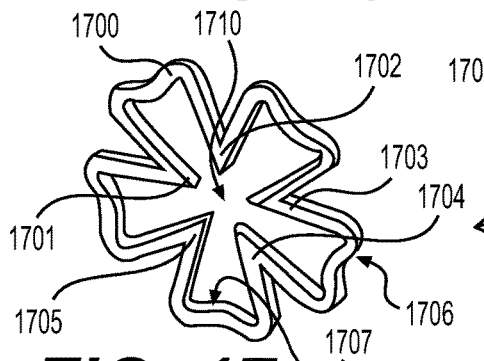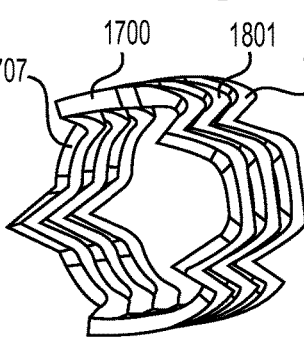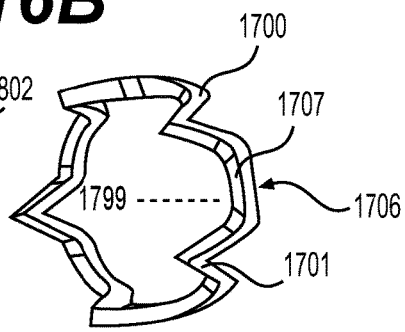
FIG. 11A  FIG. 11B  FIG. 12  FIG. 13  FIG. 14  FIG. 15  FIG. 16A  FIG. 16B  FIG. 17  FIG. 18  FIG. 19

MEDICAL SYSTEMS, DEVICES, AND RELATED METHODS

CROSS REFERENCE TO RELATED APPLICATION

This application claims priority to U.S. Provisional Application No. 63/108,590, filed Nov. 2, 2020, the entirety of which is incorporated by reference herein.

TECHNICAL FIELD

This disclosure generally relates to medical systems, devices, and related methods that may be used to treat a subject. Aspects of the disclosure relate to medical systems, devices, and methods for endoscopic medical procedures, such as manipulating and cutting tissue with one or more medical devices during resection and dissection procedures, among other aspects.

BACKGROUND

Organ walls are composed of several layers: the mucosa (the surface layer), the submucosa, the muscularis (muscle layer), and the serosa (connective tissue layer). In gastrointestinal, colonic, and esophageal cancer, lesions or cancerous masses may form along the mucosa and often extend into the lumens of the organs. Conventionally, the condition is treated by cutting out a portion of the affected organ wall. This procedure, however, may cause discomfort to patients, and pose health risks.

Physicians have adopted minimally invasive techniques called endoscopic mucosal resection (EMR) and endoscopic submucosal dissection (ESD). EMR methods are typically used for removal of small cancerous or abnormal tissues (e.g., polyps), and ESD methods are typically used for en bloc removal of large cancerous or abnormal tissues (e.g., lesions). These procedures are generally performed with an endoscope, which is a long, narrow member optionally equipped with a light, imaging equipment, and other instruments. During these procedures, the endoscope may be passed through a percutaneous incision, passed down the throat, or guided through the rectum to reach tissue targeted for resection or dissection, such as tissue having an abnormality such as a lesion or cancerous mass in an affected organ. The lesion is generally identified and marked. The lesion is subsequently removed using the same or different medical instrument.

Multiband mucosectomy (MBM) is a widely used EMR technique, which uses a modified variceal band ligator. The MBM device consists of a control handle that is attached to the proximal end of an endoscope and which is connected to a plastic cap with a number of rubber bands attached to the endoscope via a tripwire. By suctioning a mucosal lesion into the cap and then releasing a rubber band, a pseudopolyp may be created that can be resected using an electrocautery snare or other device. No submucosal lifting via needle injection or pre-looping of the snare in the cap is required for MBM.

The systems, devices, and methods of this disclosure aim to improve upon the conventional methods described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In one example, a medical device may be adapted for use with a delivery device, and the medical device may include a handle including at least one actuator; a body adapted to releasably mount to a distal portion of the delivery device, the body supporting a pair of jaws rotatably coupled to the body; and a control wire coupled to the pair of jaws and the actuator. The actuator may be configured to open and close the pair of jaws.

In other aspects, the medical device may include one or more of the following features. The handle may be configured to mount to a handle of the delivery device, and the delivery device may be an endoscope. The control wire may include a first control wire and an actuation wire coupled to the first control wire, and the actuation wire may be Y-shaped, V-shaped, or U-shaped. Proximal movement of the at least one actuator may move the control wire proximally and closes the pair of jaws. The control wire may be configured to be positioned within a working channel of the endoscope. The control wire may be positioned within a tube outside of the delivery device. The control wire may include a first control wire coupled to a first jaw of the pair of jaws and a second control wire coupled to a second jaw of the pair of jaws. The handle may include (1) a handle body on which the actuator translates, and (2) a connector configured to couple to a port of the delivery device. The actuator may be a first actuator, and the medical device may further include: at least one clip positioned around an exterior surface of the body; a tripwire releasably coupled to the at least one clip and extending from the body to the handle; and a second actuator, wherein actuation of the second actuator is configured to deploy the at least one clip from the body.

In other aspects, the medical device may include one or more of the following features. The tripwire may be positioned radially-outer from the pair of jaws relative to a central longitudinal axis of the body. The handle may include a first body, the first actuator moveably coupled to the first body; and a second body comprising a bracket configured to couple to a handle of the delivery device, wherein the second actuator is knob rotatably coupled to the second body. The handle may include a first body including a bracket configured to couple to a handle of the delivery device; wherein the first actuator is a first knob rotatably coupled to the first body; and wherein the second actuator is knob rotatably coupled to the first body. The tripwire and the control wire may be positioned within a tube extending outside of the delivery device; and the tube may be coupled to the handle. The at least one clip may include at least one of: a first clip including a first side coupled to a second side via two square pegs, wherein each of the first side and the second side includes shape memory material; a second clip including a first side and a second side, wherein the first side includes a first contoured edge portion including a sharp edge, and the second side includes a second contoured edge portion including a sharp edge, wherein the first contoured edge portion is complimentary to the second contoured edge portion; a third clip including a plurality of pointed portions pointed towards a center of a central lumen of the third clip when the third clip is in an equilibrium state, wherein the plurality of pointed portions are pointed in a distal direction when the third clip is in a loaded state on the body; and a fourth clip including a plurality of saw-toothed portions facing towards a center of a central lumen of the fourth clip when the fourth clip is in an equilibrium state, wherein the plurality of saw-toothed portions are pointed in a distal direction when the fourth clip is in a loaded state on the body. The control wire is configured to be coupled to a source of electrical energy to transmit electrical energy to the pair of jaws.

In other aspects, a medical device may be adapted for use with a delivery device, and the medical device may include a body adapted to releasably mount to a distal portion of the delivery device, the body supporting a pair of jaws rotatably coupled to the body; at least one clip positioned around an exterior surface of the body; and a tripwire releasably coupled to the at least one clip and extending proximally from the body; and a control wire coupled to the pair of jaws, wherein translation of the control wire is configured to open and close the pair of jaws to close; wherein proximal movement of the tripwire is configured to dispense the at least one clip from the body.

In other aspects, the medical device may include one or more of the following features. The body may include a coupler portion configured to mate with the distal portion of the delivery device. A tube may extend proximally from the barrel, the tripwire and the control wire may be positioned within the tube, and the tube may be positioned outside of the delivery device.

In other aspects, a medical device may be adapted for use with a delivery device, and the medical device may include: a body adapted to mount to a distal portion of the delivery device, the body supporting a pair of jaws rotatably coupled to the barrel; at least one clip positioned around an exterior surface of the body; and a handle including a first knob and a second knob and adapted to mount to a handle of the delivery device; wherein actuation of the first knob is configured to open and close the pair of jaws; and wherein rotation of the second knob is configured to dispense the at least one clip from the barrel. In some examples, the handle may further include a third knob, wherein the third knob is configured to move the tripwire to tighten or loosen the tripwire.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 2 illustrates a perspective view of an exemplary medical device, according to aspects of this disclosure.

FIG. 3 illustrates a distal portion of the exemplary medical device in FIG. 2, according to aspects of this disclosure.

FIG. 4 illustrates components of the medical device of FIG. 2, according to aspects of the disclosure.

FIG. 5 illustrates a front view of a distal portion of the medical device of FIG. 2, according to aspects of the disclosure.

FIGS. 11A-11B illustrate a front view of an exemplary clip in an equilibrium state and a loaded state, respectively, according to aspects of the disclosure.

FIG. 12 illustrates a perspective view of an exemplary clip, according to aspects of the disclosure.

FIG. 13 illustrates front and side views of an exemplary clip in an equilibrium state, according to aspects of the disclosure.

FIG. 14 illustrates a front view of an exemplary clip in a loaded state, according to aspects of the disclosure.

FIG. 15 illustrates a perspective view of an exemplary stack of clips, according to aspects of the disclosure.

FIGS. 16A-16B illustrate perspective views of an exemplary clip in an equilibrium state and a loaded state, respectively, according to aspects of the disclosure.

FIG. 17 illustrates a perspective view of an exemplary clip in an equilibrium state, according to aspects of the disclosure.

FIG. 18 illustrates a perspective view of a stack of exemplary clips, according to aspects of the disclosure.

FIG. 19 illustrates a perspective view of the exemplary clip of FIG. 17 in a loaded state, according to aspects of the disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure include devices, systems, and methods for manipulating, cutting, grabbing, ligating, and/or otherwise treating tissue. In some examples, the devices, systems and/or methods discussed herein may be utilized during endoscopic mucosal resection (EMR) and/or endoscopic submucosal dissection (ESD) procedures. In examples, EMR and ESD include endoluminal placement of one or more devices for grasping and cutting tissue proximate to a target area within the body of a patient. Placement of the one or more medical devices may be via a catheter, scope (endoscope, bronchoscope, colonoscope, gastroscope, duodenoscope, etc.), tube, or sheath, inserted into the GI tract via a natural orifice or incision. The orifice can be, for example, the nose, mouth, or anus, and the placement can be in any portion of the GI tract, including the esophagus, stomach, duodenum, large intestine, or small intestine. Placement also can be in other organs reachable via the GI tract. The patient's tissue may be grasped using suction from one or more medical devices and/or a grasper, and then the tissue may be cut by a cutting device for subsequent removal from the patient's body. Although EMR and ESD are discussed herein, the disclosure is not so limited. Embodiments of the disclosure include devices and systems that may be used in any suitable procedure in any body lumen or organ.

Reference will now be made in detail to examples of this disclosure described above and illustrated in the accompanying drawings. Wherever possible, the same reference numbers will be used throughout the drawings to refer to the same or like parts.

Figure 1:
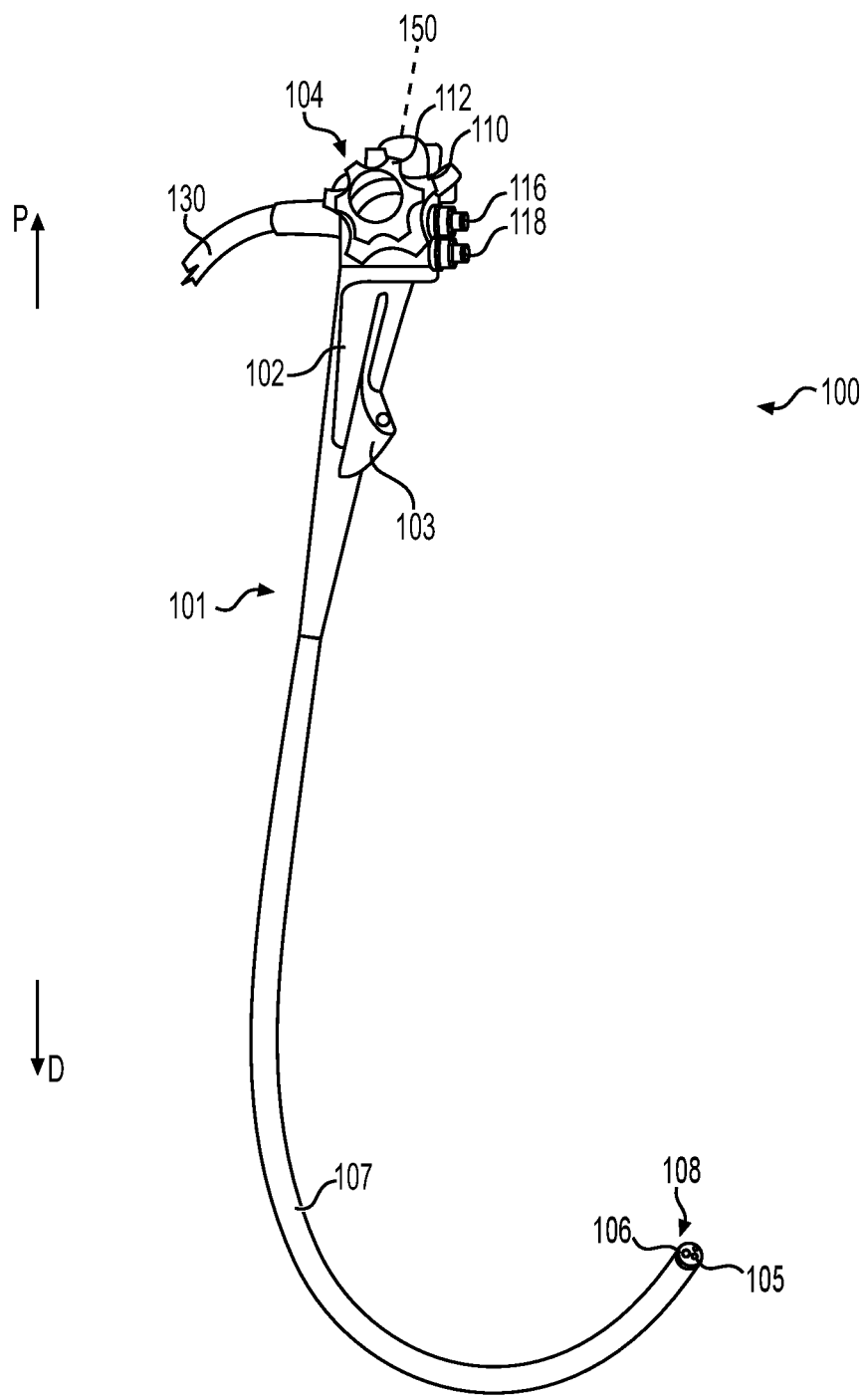
FIG. 1 illustrates a perspective view of a medical device, according to aspects of this disclosure.

FIG. 1 illustrates a perspective view of an exemplary medical device assembly 100 including an endoscope 101. Although medical device assembly 100 is shown with endoscope 101, any other similar insertion device may be used in medical device assembly 100, such as a bronchoscope, colonoscope, gastroscope, duodenoscope, etc. Endoscope 101 may include a handle 102, actuators 104, and a body 107 extending from handle 102 to a distal end 108. A working channel 106 may extend from a working channel port 103 positioned on the handle 102 to an opening at distal end 108. Distal end 108 of endoscope 101 may also include a camera 105, and movement of distal end 108 and functionality of camera 105 may be controlled via one or more actuators 104 on handle 102. Actuators 104 may include knob actuators 110, 112, button actuators 116, 118, and any other types of actuators known in the art. An umbilicus 130 may connect endoscope 101 to a control unit, a fluid source, a suction source, and/or other exterior devices such as a monitor for viewing images from camera 105. A control unit connected to umbilicus may control any aspect of endoscope 101, such as camera 105. Endoscope 101 may have a central longitudinal axis 150 extending longitudinally through a central portion of handle 102 and body 107.

FIG. 2 illustrates a perspective view of an exemplary medical device 200 in a partially disassembled state for illustration purposes. Medical device 200 may include a handle 202, a connector 204 coupled to a distal end of the handle 202, a tube 207 extending distally from connector 204, and a distal portion 206. Distal portion 206 may include a body 210, a coupler 208, a pair of jaws 212, 214, and a control wire 216. Control wire 216 is shown extending through coupler 208 for illustration purposes only, and, in at least some embodiments, would extend through tube 207, connector 204, and handle 202 when medical device 200 is fully assembled. Control wire 216 may be coupled to actuator 222 of handle 202 via fastener 228. In some examples, a portion of control wire 216 may extend through side tube 226. Handle 202 may be connected to an electrical supply through fastener 228 to electrify control wire 216 and jaws 212, 214 and provide a means for electrical cautery. Handle 202 may include a ring portion 220 at a proximal end of handle 202, and ring portion 220 may be configured to receive one or more fingers of a user. A handle body 225 may extend distally from ring portion 220, and actuator 222 may be cylindrical and configured to move proximally and distally relative to handle body 225. Actuator 222 may include a convex radially-outer surface relative to a longitudinal axis 299 of handle 202, and may be configured to accommodate one or more of a user's fingers. A reference mark 224 may be on an exterior surface of handle 202. Actuator 222 may receive fastener 228 and side tube 226, and may be configured to couple to a proximal portion of control wire 216. Side tube 226 may be configured to receive a portion of control wire 216 proximal of fastener 228, may be flexible, and may be configured to protect a user's fingers and hand from an electrified control wire 216.

Connector 204 may be coupled to a distalmost end of handle 202 and may be coupled to a proximal end of tube 207. Connector 204 may be Y-shaped and may include a main body 203 and a side port 205. Each of main body 203 and side port 205 may be substantially cylindrical. Main body 203 may be configured to receive control wire 216, and side port 205 may be configured to provide access to tube 207, such as for insertion of other medical devices into tube 207. Tube 207 may be substantially the same length as medical device 101, and may connect distal portion 206 with connector 204. In some examples, medical device 200 may not include connector 204, and tube 207 may connect handle 202 with distal portion 206. Tube 207 may be flexible and may be made of any suitable material known in the art, such as a polymer or other similar material.

FIG. 3 shows a magnified view of distal portion 206 in FIG. 2. Body 210 may be cylindrical (shown in FIG. 3) and may include a central lumen 305 extending from a distal opening 244 of body 210. In other examples, body 210 may be hexagonal, octagonal, polygonal, oval shaped, or any other suitable shape. Coupler 208 may be fixedly coupled to a proximal end of body 210. Coupler 208 may be an elastomer and may be configured to extend around an exterior surface of distal portion 108 of endoscope 101. Coupler 208 may be cylindrical, hexagonal, octagonal, polygonal, oval shaped, or any other suitable shape. Coupler 208 may be configured to cap a distal end of endoscope 101 (via a friction fit, for example), such that distal portion 206 couples to distal portion 108 of endoscope 101. The circumference of lumen 305 may be larger than the circumference of distal portion 108. In some examples, body 210 and/or coupler 208 may be transparent or semi-transparent. Tube 207 may be coupled to a radially-outward facing surface 327 relative to a central longitudinal axis 399 of body 210. A central lumen extending through the length of tube 207 may connect to lumen 305 of body 210.

Pair of jaws 212, 214 may be positioned within lumen 305 and coupled to an inner wall 345 of body 210. Inner wall 345 may be a radially-inward facing surface of body 210 relative to axis 399. Jaws 212, 214 may be rotatably coupled to molded hinges on inner wall 345. In other examples, jaws 212, 214 may be coupled to inner wall 345 via one or more fasteners (e.g. a rivet, screw, pivot pin, or other mechanism), and jaws 212, 214 may be rotatable about one or more shafts of the one or more fasteners. Each jaw 212, 214 may be rotatable relative to hinge points 306, 307.

FIG. 4 illustrates jaw 212 removed from medical device 200. Jaw 212 may include apertures 401, 402 configured to receive a molded hinge of inner wall 345 or a fastener. Jaw 212 may be curved, arch shaped, and/or semi-circular. In other examples, jaw 212 may be V-shaped, M-shaped, irregularly curved, or any other suitable shape. Jaw 212 may include a sharp edge 405 configured to cut tissue. In some examples (not shown), edge 405 may be jagged, teeth-shaped, include a series of sharp points, or serrated. In other examples, edge 405 may be dull and configured to grab tissue but not cut tissue. In some examples, edge 405 of jaw 212 may be configured to mate with an opposing edge of jaw 214. Jaw 212 may include a proximal arm 407, and proximal arm 407 may extend proximally relative to aperture 402. Proximal arm 407 may include an aperture 408 extending through proximal arm 407, and aperture 408 may be configured to receive an actuation wire 420. As shown in FIG. 4, actuation wire 420 may include a Z-shaped bend, at least a portion of which is configured to be positioned within lumen 408, to secure wire 420 to jaw 212.

Actuation wire 420 may be a single wire and, as shown in FIG. 3, may be Y-shaped, V-shaped, U-shaped, or any other suitable shape. As shown in FIG. 3, actuation wire 420 may have a first end coupled to proximal arm 407 of jaw 212, may extend through a first guide hole or guide clip 310, through a distal loop 330 of control wire 216, through a second guide hole or guide clip 312, and may be coupled to a proximal arm 318 of jaw 214 at a second end of actuation wire 420. Actuation wire 420 may include a Z-shaped bend 420 at each of the first and second ends of actuation wire 420. Guide holes or guide clips 310, 312 may be positioned on inner wall 345 of body 210, and may extend radially-inward towards central longitudinal axis 399 of body 210. Guide holes or guide clips 310, 312 may maintain a specific direction of movement of actuation wire 420, may provide leverage to actuation wire 420, and/or may limit the maximum and/or minimum rotation of jaws 212, 214. In some examples, guide clips 310, 312 may be cylindrical, and in other examples guide clips may be U-shaped and configured to be clipped or snapped into position around actuation wire 420. Each of the first and second ends of actuation wire 420 may be biased to move radially-outward from central longitudinal axis 399 when positioned within lumen 305 of body 210. In some examples, actuation wire 420 may be coupled to control wire 216 at a midpoint of actuation wire 420, and actuation wire 420 may include a ring portion 332 at a midpoint of actuation wire 420. Ring portion 332 may be configured to receive control wire 216 and/or a coupler attached to control wire 216. In some examples, control wire 216 may be inserted through ring portion 332 and then a crimp sleeve or lock sleeve may be positioned over control wire 216 to couple control wire 216 to ring portion 332. In other examples, control wire 216 may be soldered, glued, or otherwise directly coupled to actuation wire 420, and actuation wire 420 may not include ring portion 332. In some examples, actuation wire 420 may include two separate wires and a ring portion 332, with one wire extending from jaw 212 to ring portion 332 and another wire extending from jaw 214 to ring portion 332.

By providing actuation wire 430 with ring portion 332, medical device 200 may position control wire 216 through a working channel 106 of endoscope 101, then position control wire 216 through ring portion 332 of actuation wire 420, followed by positioning a lock sleeve or other coupling mechanism around control wire 216 to couple control wire 216 to ring portion 332. In some examples when control wire 216 may extend through tube 207, a portion of actuation wire 420 may extend within tube 207 and actuation wire 420 may curve towards tube 207. Ring portion 332 may allow control wire 216 to move actuation wire 420 proximally and distally when control wire 216 is moved proximally and distally, respectively.

FIG. 5 illustrates a front view of distal portion 206 of medical device 200. As shown in FIG. 5, jaws 212, 214 are in a completely closed position and edge 405 of jaw 212 contacts a like edge of jaw 214. In some examples, jaws 212, 214 may have a limited range of motion, and a user may not be able to completely close jaws 212, 214 together. In some examples (as shown in FIG. 5), jaws 212, 214 may be transparent or semi-transparent, to permit visualization distal of jaws 212, 214 via an imager of endoscope 101. Inner wall 345 may include planar portions 501, 502 configured to be adjacent to jaws 212, 214, and curved portions 503, 504. In some examples, planar portions 501, 502 may each include a protrusion (not shown) configured to mate with one of apertures 401, 402 of jaws 212, 214; and each protrusion may be sized to extend through an aperture 401, 402 of both jaws 212, 214, and act as a pivot point for jaws 212, 214. In other examples, planar portions 501, 502 may not include protrusions, and jaws 212, 214 may be coupled to planar portions 501, 502 via a coupler, such as a screw, rivet, or pivot pin.

In some examples, medical device 200 may include a sheath or protective cover (not shown) that may extend from distal portion 206 to handle 202, and may facilitate gathering or bundling tube 207 and shaft 107 of endoscope 101.

In an exemplary embodiment, control wire 216 may be coupled to actuation wire 420, extend through tube 207, through connector 203, and into handle 202. Control wire 216 may be coupled to actuator 222 via fastener 228. Fastener may also be connected to an electrical power source and supply electrical energy to control wire 216, actuation wire 420, and jaws 212, 214. In some examples, a user may position actuator 222 at reference mark 224 on handle body 225, and then pull control wire 216 taught such that jaws 212, 214 are in a closed position before fastening control wire 216 to actuator 222. After fastening wire 216 to actuator 222, a user may move actuator 222 proximally relative to handle 202 to cause the edges of jaws 212, 214 to move together, closing jaws 212, 214. When a user moves actuator 222 proximally, control wire 216 will move proximally and pull actuation wire 420 proximally, which moves proximal arms 407, 318 proximally and causes jaws 212, 214 to rotate about hinge points 306, 307. When a user subsequently moves actuator 222 distally relative to handle 202, control wire 216 moves distally and pushes actuation wire 420 distally. The distal movement of actuation wire 420 moves proximal arms 318, 407 distally and causes jaws 212, 214 to rotate about hinge points 306, 307, and jaws 212, 214 move towards each other to close or clamp down. When control wire 216 is positioned within tube 207, a user may couple distal portion 206 to endoscope 101 and be ready to operate device, which may facilitate operation of medical device 200 and reduce procedure time.

In another exemplary embodiment, control wire 216 may be positioned outside of tube 207. In this embodiment, control wire 216 may extend through a working channel 106 of endoscope 101 during operation, and may be connected to handle 202 after exiting working channel port 103. This embodiment does not require tube 207. When tube 207 is omitted from medical device 200, connector 204 may be directly coupled to working channel port 106. By removing tube 207 from medical device 200, the overall size of medical device 200 is reduced which may reduce trauma to a patient during operation and facilitate movement of endoscope 101 and medical device 200 through a body. Once control wire 216 is positioned within working channel 106, and coupled to actuator 222 of handle 202, a user may operate the device in the same manner as the previously described embodiment.

Figure 6:
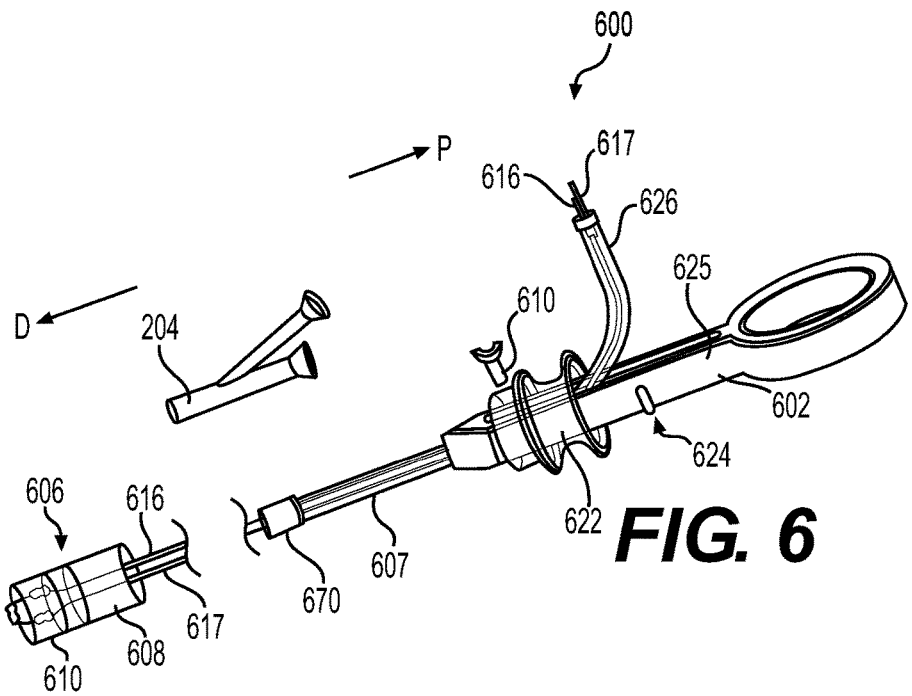
FIG. 6 illustrates a perspective view of an exemplary medical device, according to aspects of this disclosure.

FIG. 6 shows another exemplary medical device 600, with a portion of the device omitted. Medical device 600 may include a handle 602, actuator 622, connector 607, distal portion 606, and control wires 616, 617. Any of the features discussed hereinabove regarding medical device 200 may be incorporated into medical device 600. Connector 204 is also shown in FIG. 6 and may replace connector 607 in some embodiments of medical device 600. Medical device 600 may include two control wires 616, 617, one extending from each jaw 612, 614, respectively, through connector 607 into handle 602 and coupled to actuator 622. As shown in FIG. 6, excess portions of control wires 616, 617 may be positioned within side tube 626 after control wires 616, 617 are pulled taught and coupled to actuator 622 via fastener 610. Similar to medical device 200, a user may position actuator 622 at guide marker 624 on handle body 625 before coupling control wires 616, 617 to actuator 622. Connector 607 may include an adapter 670 configured to mate with (e.g. screw into, snap-fit couple to, etc.) working channel port 103 of endoscope. Portions of control wires 616, 617 are omitted from FIG. 6 for illustration purposes only. Distal portion 606 of medical device 600 may include body 610 and coupler 608 which may have any of the above-described features of body 210 and coupler 208.

Figure 7:
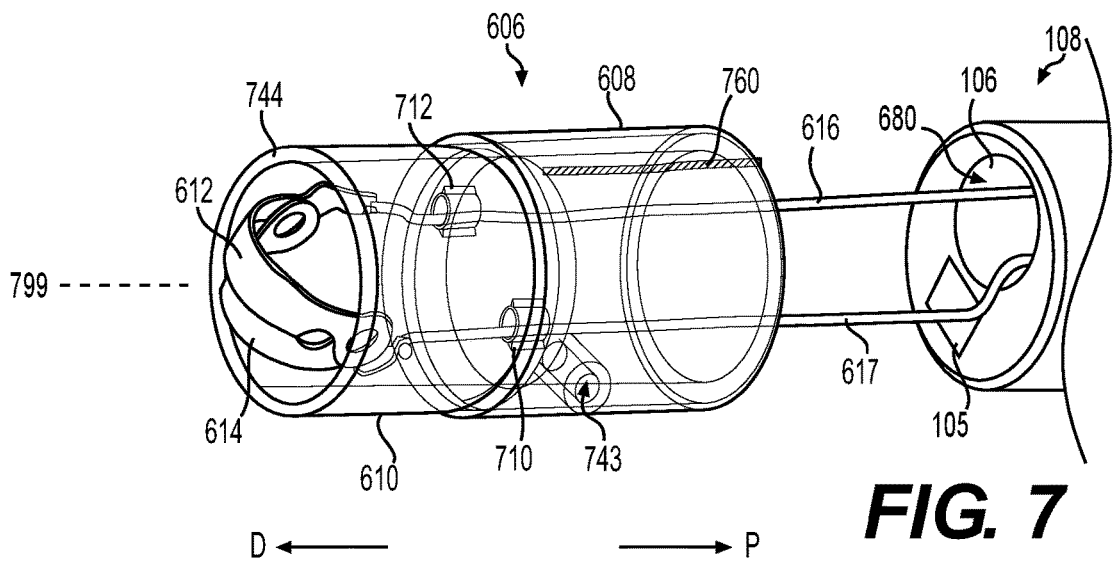
FIG. 7 illustrates a distal portion of the medical device of FIG. 6, according to aspects of the disclosure.

FIG. 7 illustrates distal portion 606 of medical device 600, with control wires 616, 617 extending from distal portion 606 into working channel 106 of endoscope 101. Distal portion may include jaws 612, 614 rotatably coupled to body 610, and body 610 may include guide clips 710, 712 for receiving control wires 616, 617. In some examples (as shown in FIG. 7), jaws 612, 614 may extend distally from a distalmost surface 744 of body 610 when jaws 612, 614 are in a closed position. Tube input port 743 may be positioned on a radially-outer surface of body 610 or connector 608, relative to central longitudinal axis 799 of distal portion 606, and may be configured to receive a tube similar to tube 207. In some examples, distal portion 606 may not include tube input port 743. In other examples, both control wires 616, 617 may be positioned within a tube coupled to tube input port 743 and extend to handle 602 outside of endoscope 101. Coupler 608 may include an alignment marker 760 on a radially-outer surface relative to central longitudinal axis 799 of distal portion 606. Alignment marker 760 may facilitate alignment of distal portion 606 with distal portion 108 of endoscope 101 when a user couples distal portion 606 to distal portion 108.

In operation, a user may first cover control wires 616, 617 temporarily with a sheath to facilitate moving control wires 616, 617 through working channel 106. In other examples, control wires 616, 617 may not be sheathed and may be directly inserted into a distal opening 680 of working channel 106 to position control wires 616, 617 within working channel 106. Once control wires 616, 617 are pushed through working channel 106 and exit working channel port 103, a user may remove any temporary sheath positioned over control wires 616, 617, and may then insert control wires 616, 617 into handle 602, and specifically first through adapter 670. At this point, the user may also couple distal portion 606 to distal portion 108 by positioning coupler 608 around an exterior surface of distal portion 108; and then couple connector 607 to working channel port 103 via adapter 670. Alignment marker 760 may facilitate aligning the positioning of jaws 612, 614 relative to camera 105. The user may then position actuator 622 at guide marker 624, pull guide wires 616, 617 taught such that jaws 612, 614 are in a closed position, and fasten control wires 616, 617 to actuator 622 via fastener 610. Extra portions of control wires 616, 617 proximal of actuator 622 may be positioned within side tube 626. In some examples, the user may then connect fastener 610 to a source of electrical power to supply electrical energy to control wires 616, 617 and jaws 612, 614. In other examples, handle 602 may include an additional actuator (e.g. button, dial, etc.) to selectively apply electrical energy to control wires 616, 617. The user may then move actuator 622 distally relative to handle body 625 to open jaws 612, 614; and move actuator 622 proximally relative to handle body 625 to close jaws 612, 614. In some examples, a user may apply air suction (aspiration) to working channel 106 to pull tissue into body 610 (with jaws 612, 614 in an open position) and allow jaws 612, 614 to cut tissue. In some examples, one of actuators 116, 118 may actuate a suction source connected to endoscope 101 via umbilicus 130 and apply suction to distal portion 108 of endoscope 101, such as via working channel 106. In other examples, air suction may be applied to a tube connected to tube port 743. Any of the components of medical devices 200 and 600 may be transparent, which may facilitate visualization of a target area using camera 105 and/or increase a field of view of camera 105 during operation.

Figure 8:
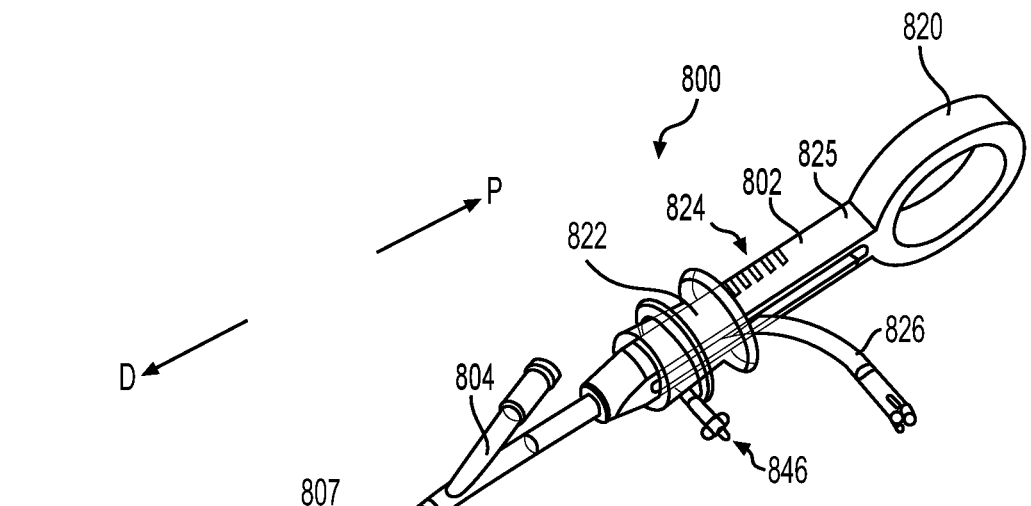
FIG. 8 illustrates a perspective view of an exemplary medical device, according to aspects of this disclosure.

FIG. 8 illustrates a perspective view of a partially assembled, exemplary medical device 800. Medical device 800 may include any of the features described herein in connection with any of the other exemplary medical devices 200, 600. Medical device 800 may be configured to deploy clips 891-896. Medical device 800 may include handle 802, connector 804, tube 807, and distal portion 806. Handle 802 may include actuator 822, side tube 826, fastener 846, proximal loop portion 820, and a plurality of markings 824. Distal portion 806 may include body 810, coupler 808, one or more clips 891-896 (shown in FIG. 9), a trip wire 833, and cord 838. In some examples, clips 891-896 may be spring loaded, may include a shape-memory material, and may be made of metal, polymer, nitinol, or any other suitable material. Clips 891-896 will be discussed in more detail below with relation to FIGS. 11A-21. An outer sheath 835 may be positioned around a portion of body 810, connector 808, and tube 807. Outer sheath 835 may facilitating shielding tube 807 and coupler 808 during operation, and may prevent unnecessary movement of tube 807 relative to coupler 808. Outer sheath 835 may also facilitate insertion of medical device 800 coupled to endoscope 101 into a body. Coupler 808 may couple to a distal portion 108 of endoscope 101 in the same manner as described above in relation to couplers 208, 608. Cord 838 may be coupled to each of clips 891-896 and extend within lumen 805 of body 810 and connector 808. Cord 838 may be coupled to tripwire 833. In some examples, cord 838 may include a loop 839 and tripwire 833 may include a hook 898 at a distalmost end of tripwire 833, and the hook of tripwire 833 may be positioned through loop 839. FIG. 10 shows a magnified view of cord 838 with loop 839 and tripwire 833 with hook 898. Hook 898 may facilitate coupling tripwire 833 to cord 838. Once hook of trip wire 833 is positioned within loop 839, a lock sleeve 841, which is shown proximal to loop 839 and hook 898 in FIG. 10, may be positioned over loop 839 and hook of tripwire 833 to fixedly couple tripwire 833 to cord 838. Any of the actuation wires or tripwires discussed in this disclosure may include a cable, a suture, or any other elongate member capable of transferring a force from a handle/actuator to a distal tool (jaws, clips, etc.).

Lock sleeve 841 is shown proximal to loop 838 in FIGS. 8 and 10, and lock sleeve 841 would be slid down tripwire 833 and over loop 839 to fixedly couple cord 838 to tripwire 833. In other examples, medical device 800 may not include lock sleeve 841, and tripwire 833 may be coupled to cord 838 via an adhesive, a coupler, or any other coupling means known in the art. In a fully assembled state, tripwire 833 may extend through tube 807 and connector 804, and be coupled to actuator 822. Fastener 846 may couple tripwire 833 to actuator 822. In other examples, tripwire 833 may be positioned within working channel 106 of endoscope 101, tube 807 may be omitted from medical device 800, and connector 804 may be coupled to working channel port 103.

Figure 9:
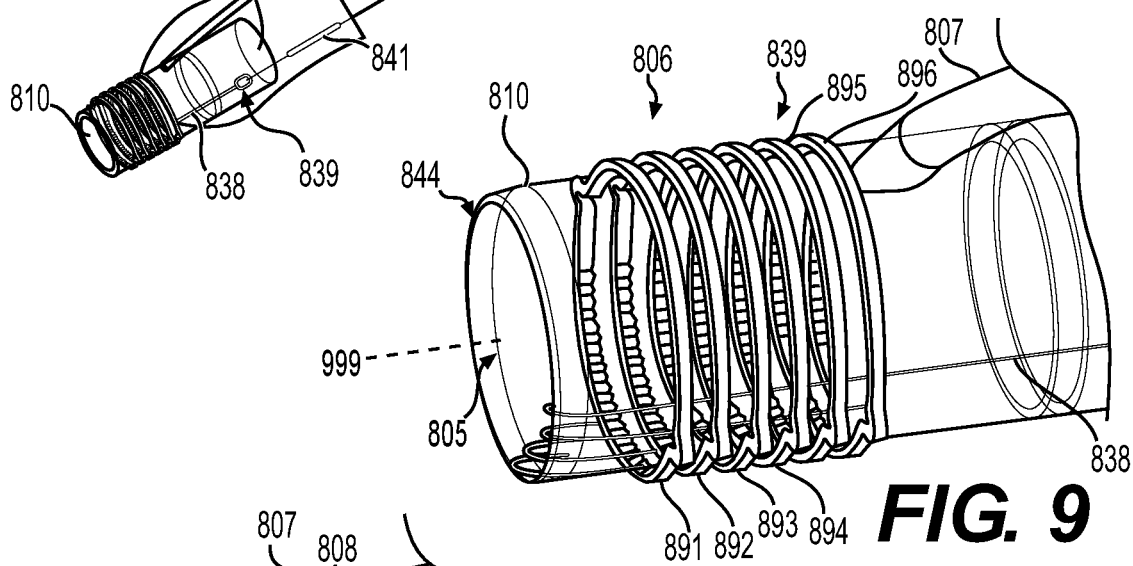
FIG. 9 illustrates a distal portion of the medical device of FIG. 8, according to aspects of the disclosure.
Figure 10:
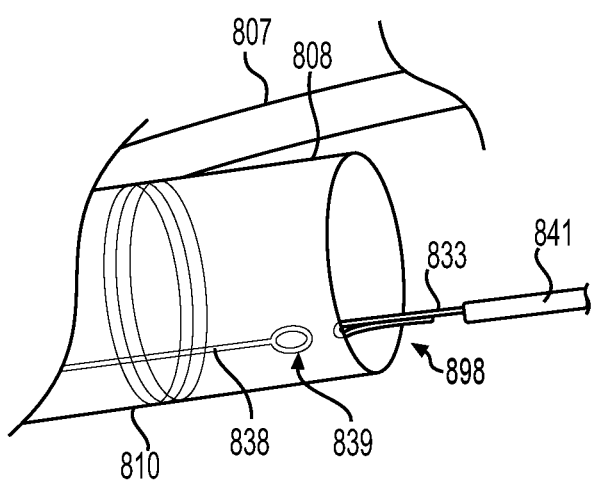
FIG. 10 illustrates a partially-disassembled distal portion of the medical device of FIG. 8, according to aspects of the disclosure.

FIG. 9 shows a magnified view of distal portion 806 including body 810, tube 807, cord 838, and clips 891-896. Cord 838 may be fixedly coupled to each of clips 891-896, and a prescribed length of cord 838 may be wrapped around an exterior portion of body 810 between points in which cord 838 is coupled to each clip 891-896. In some examples, cord 838 may be releasably coupled to each clip via a knot, an adhesive, a coupler, a loop of cord 838, and/or any other coupling means known in the art. A clip 891-896 may be released, deployed, or dispensed from body 810 when cord 838 pulls the clip distally beyond the distalmost surface 844 of body 810.

Figure 28:
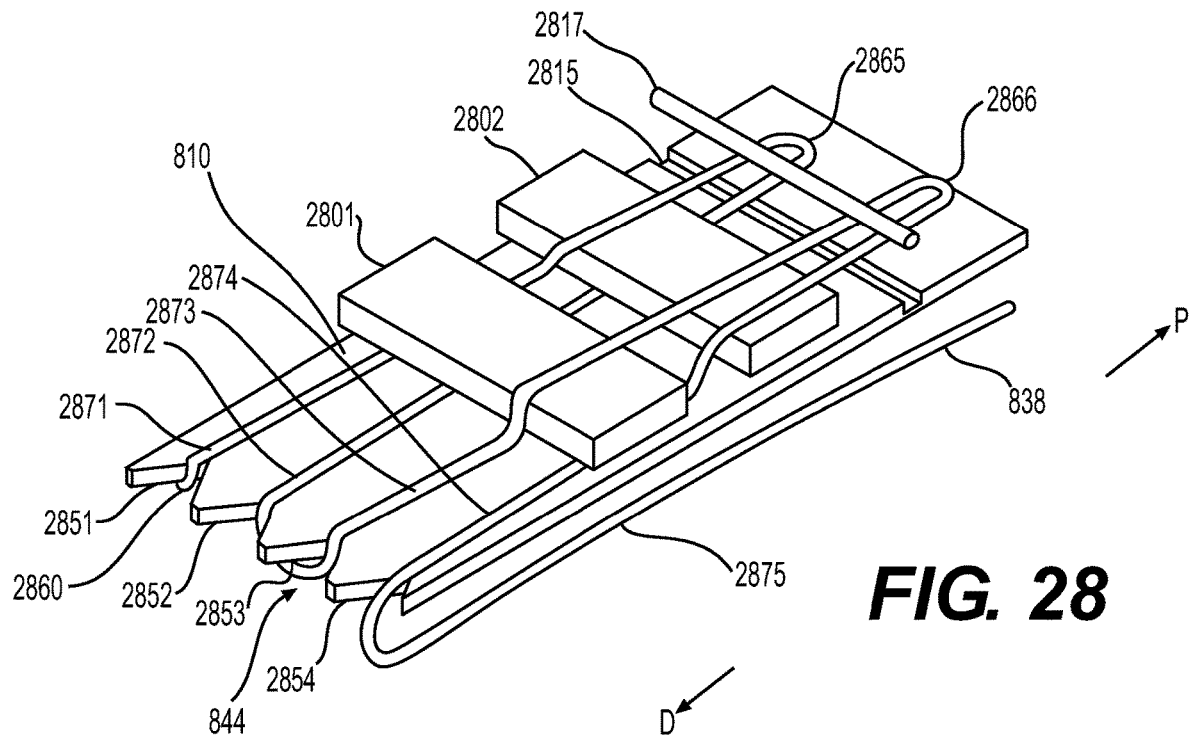
FIG. 28 illustrates a magnified portion of a medical device, according to aspects of the disclosure.
Figure 29:
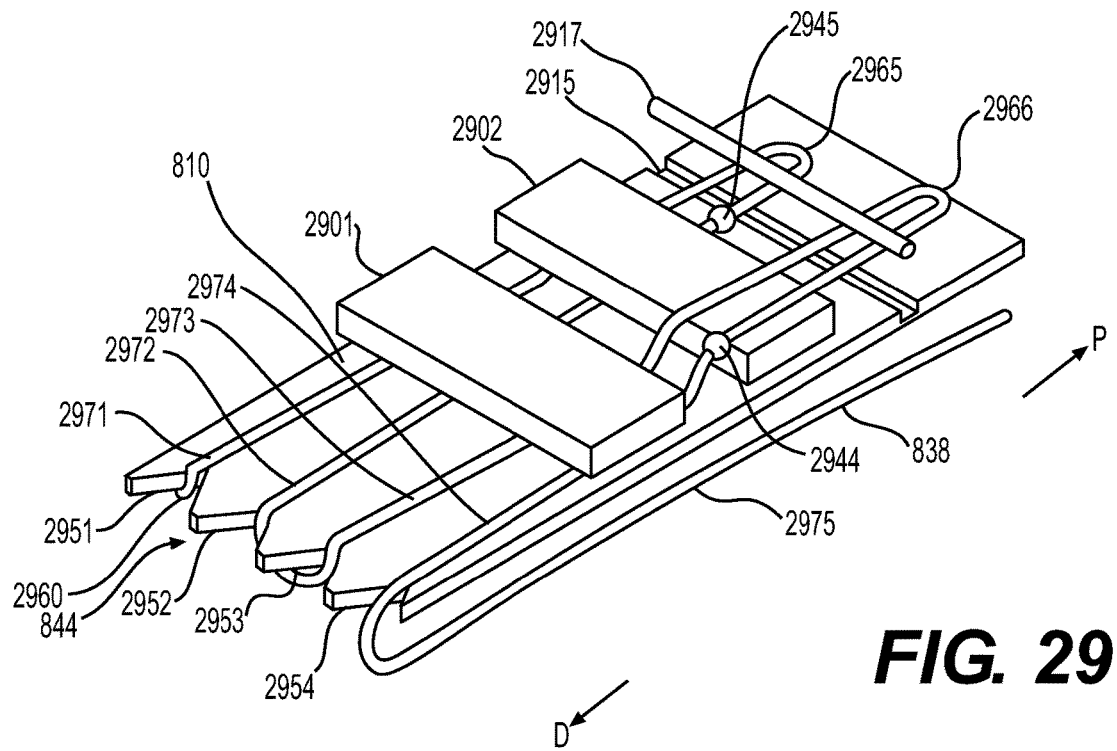
FIG. 29 illustrates a magnified portion of a medical device, according to aspects of the disclosure.

FIGS. 28 and 29 illustrate two different exemplary configurations of cord 828 coupled to exemplary clips 2801, 2802. FIG. 28 shows a magnified view of a portion of body 810 with exemplary portions of clips 2801, 2802 positioned around body 810. Portions of body 810, clips 2801, 2802, o-ring 2817, and cord 838 are removed for illustration purposes. In the embodiment of body 810 shown in FIG. 28, distalmost surface 844 of body 810 may include a series of notches 2851-2854, and cord 838 may be positioned within each of the series of notches 2851-2854. An elastic o-ring 2817 or other elastic member may be positioned around body 810 and may be positioned within a groove 2815 extending circumferentially around an exterior surface of body 810 (FIG. 28 shows o-ring 2817 above groove 2815 for illustrative purposes only). Elastic o-ring 2817 may be positioned proximal to each clip 2801, 2802. The distalmost end 2860 of cord 838 may be coupled to a portion of body 810 via a knot, glue, tension in cord 838, a coupler, or any other means known in the art. A first length 2871 of cord 838 may extend proximally from distalmost end 2860 to first loop 2865 of cord 828. First length 2871 may be positioned underneath clip 2801 and o-ring 2817, and may extend over (or radially-outer relative to central longitudinal axis 999 of body 810) clip 2802. A second length 2872 of cord 838 may extend from loop 2865 to notch 2852, and may be positioned underneath, or radially-inner relative to central longitudinal axis 999 of body 810 from, o-ring 2817 and clips 2801, 2802. A third length 2873 may extend from notch 2853 over clips 2801, 2802, and underneath o-ring 2817 to loop 2866; and a fourth length 2874 may extend from loop 2866 underneath o-ring 2817, over clip 2802, and underneath clip 2801 to notch 2854. A fifth length 2875 of cord 838 may extend from notch 2854 to tripwire 833 (not shown in FIG. 28).

Each length 2871-2874 may be the same distance such that a user may move an actuator coupled to tripwire 833 the same distance, or rotate an actuator coupled to tripwire 833 the same number of degrees, to deploy a single clip 2801-2802. When a user pulls tripwire 833 proximally, cord 838 may be pulled proximally and loop 2866 may move distally relative to body 810. When loop 2866 moves distally, loop 2866 will travel underneath o-ring 2817 and over clip 2802 until loop meets clip 2801. Once loop 2866 meets clip 2801, clip 2801 may be pulled distally by loop 2866 until clip 2801 is released from body 810 and moves distal relative to distalmost surface 844. For purposes of this disclosure, cord 838 may be releasably coupled to a clip 2801, 2802, 2901, 2902 when cord 838 is in contact with a clip 2801, 2802, 2901, 2902 and/or positioned between a clip 2801, 2802, 2901, 2902 and body 810.

FIG. 29 shows an exemplary configuration of cord 828 coupled to exemplary clips 2901, 2902. FIG. 29 shows a magnified view of a portion of body 810 with exemplary portions of clips 2901, 2902 positioned around body 810. Portions of body 810, clips 2901, 2902, o-ring 2917, and cord 838 are removed for illustration purposes. In this embodiment of body 810 shown in FIG. 29, distalmost surface 844 of body 810 may include a series of notches 2951-2954, and cord 838 may be positioned within each of the series of notches 2951-2954. An elastic o-ring 2917 or other elastic member may be positioned around body 810 and may be positioned within a groove 2915 extending circumferentially around an exterior surface of body 810. Elastic o-ring 2917 may be positioned proximal to each clip 2901, 2902. The distalmost end 2960 of cord 828 may be coupled to a portion of body 810 via a knot, glue, tension in cord 838, a coupler, or any other means known in the art. A first length 2971 of cord 838 may extend proximally from distalmost end 2960 to first loop 2965 of cord 838. First length 2971 may be positioned underneath clips 2901, 2902 and o-ring 2817. A second length 2972 of cord 838 may extend from loop 2965 to notch 2952, and may be positioned underneath, or radially-inner relative to central longitudinal axis 999 of body 810 from, o-ring 2917 and clips 2901, 2902. A bead 2945 may be fixedly coupled to length 2972 of cord 838, and bead 2945 may be positioned proximal to clip 2902. A third length 2973 of cord 838 may extend from notch 2953 underneath clip 2901, over clip 2902, and underneath o-ring 2917 to loop 2966; and a fourth length 2974 may extend from loop 2966 underneath o-ring 2917, over clip 2902, and underneath clip 2901 to notch 2954. A bead 2944 may be fixedly coupled to length 2974, and bead 2944 may be positioned between clip 2901 and clip 2902. A fifth length 2975 of cord 838 may extend from notch 2954 to tripwire 833 (not shown in FIG. 29).

Each length 2971-2974 may be the same distance such that a user may move an actuator coupled to tripwire 833 the same distance, or rotate of an actuator coupled to tripwire 833 the same number of degrees, to deploy a single clip 2901-2902. When a user pulls tripwire 833 proximally, cord 838 may be pulled proximally, and loop 2966 and bead 2944 may move distally relative to body 810. Once bead 2944 engages clip 2901 (abuts with or comes into contact with), clip 2901 may be pushed distally by bead 2944 until clip 2901 is released from body 810 and moves distal relative to distalmost surface 844. Once clip 2901 is released from body 810, the user may continue to pull cord 838 proximally, causing length 2972 to be moved distally relative to body 810 and bead 2945 to engage clip 2902. Bead 2945 may then push clip 2902 distally as length 2972 moves distally until clip 2902 is pushed distal to body 810 and released. In other examples, beads 2944, 2945 may be replaced with knots, crimps, tubes, or similar components.

FIGS. 28 and 29 illustrate two different methods for deploying clips from medical device 800 using cord 838. Other methods of deployment of clips may be found in U.S. patent application Ser. No. 14/499,859, filed on Sep. 29, 2014; U.S. patent application Ser. No. 14/737,733, filed Jun. 12, 2015; U.S. patent application Ser. No. 09/157,577, filed Sep. 21, 1998; and U.S. patent application Ser. No. 09/838,297, filed Apr. 20, 2001.

In operation, when tripwire 833 is positioned within tube 807 and fastened to actuator 822, a user may first couple coupler 808 to distal portion 108 of endoscope 101. The user may the position distal portions 108, 806 proximate to a target site within a body of a patient. The user may then release one of clips 891-896 from body 810 by moving actuator 822 proximally relative to handle body 825. In some examples, the user may move actuator 822 proximally to align with a distalmost marking 824 on handle 802 to release a first clip 891 from body 810. In some examples, actuator 822 may be a ratcheted actuator, may be limited to only move in a proximal direction and prevented from moving distally, and may provide an audible click after the user positions actuator 822 in alignment with a marking 824, to release a clip. Clip 891 may be spring loaded and may compress onto tissue when released from body 810. To deploy another clip 892, the user may again move actuator 822 proximally and into alignment with the next marking 824 on handle 802.

FIG. 11A shows an end of an exemplary clip 1191 in an equilibrium state. Clip 1191 may include a central lumen 1199. Clip 1191 may be manufactured by laser cutting or stamping clip 1191 from a nitinol sheet. Sides of clip 1191 may be pulled in opposing lateral directions 1181, 1182 to open lumen 1199 and transition clip 1191 from an equilibrium state (shown in FIG. 11A) to an expanded/loaded state (shown in FIG. 11B). For example, when a loaded clip 1191 is release from body 810, the clip will return towards its equilibrium state (shown in FIG. 11A). Lumen 1199 may be sized such that in a loaded state, clip 1191 fits around body 810 of medical device 800.

FIG. 12 illustrates another embodiment of a clip 1200 in a loaded state. Clip 1200 may be made in a single piece of nitinol or other shape memory material as shown in FIG. 13. FIG. 13 shows a top view 1302 and an end view 1303 of clip 1200 in an equilibrium state. Top portion 1285 of clip 1200 may be pulled in a first lateral direction 1281, and bottom portion 1286 may be pulled in a second lateral direction 1282 which is opposite the first lateral direction 1281. FIG. 14 shows an alternative embodiment of a clip 1400 similar to clip 1200, however pins 1404, 1405 are used to couple each side 1402, 1403 of clip 1400 together. Pins 1404, 1405 may have a square cross-sectional shape to prevent sides 1402, 1403 from losing their closure elasticity (or tendency towards the equilibrium state). In some examples, pins 1404, 1405 may act as torsional springs. Pins 1404, 1405 may be made of nitinol or other shape memory materials. FIG. 15 shows a plurality of clips 1200 stacked on top of each other with lumens 1201 aligned along a central axis 1299.

FIGS. 16A and 16B illustrate an exemplary clip 1600 including a contoured edge portion 1603. FIG. 16A shows clip 1600 in an equilibrium state, and FIG. 16B shows clip 1600 in a loaded state similar to the loaded state of clip 1200. Contour edge portion 1603 may include a first contoured edge 1606 on a first side 1601 of clip 1600, and a second contoured edge 1607 on a second side 1602 of clip 1600. Each contoured edge 1606, 1607 may include sharp or dull teeth, which may be used to cut or to grip tissue. Clip 1600 may be made of a single piece of flat nitinol or other shape memory material, or may be made of more than one piece of material. In some examples, first side 1601 may be moved in a first lateral direction 1681, and second side 1602 may be moved in a second lateral direction 1682 to position clip 1600 around body 810. In addition, first contoured edge 1606 may face a proximal direction and second contoured edge 1607 may face a distal direction when positioned around body 810.

FIGS. 17-19 illustrate another exemplary clip 1700. FIG. 17 shows clip 1700 in an equilibrium state with five pointed portions 1701-1705 pointed towards a center of central lumen 1710 of clip 1700. Pointed portions 1701-1705 may be sharp and may be configured to cut tissue, may be dull and configured to grab tissue but not pierce tissue, may be rounded, may be flat-ended, or any combination thereof. Although clip 1700 is shown with five pointed portions 1701-1705, any number of pointed portions may be included in clip 1700. In an equilibrium state, surface 1707 of clip 1700 may be directed radially-inward towards a central longitudinal axis 1799 of lumen 1702. FIG. 19 shows clip 1700 in a loaded state. Portions of clip 1700 may be rotated relative to positions of those portions in the equilibrium state, to attain the loaded state. In the loaded state, surface 1707 faces distally and in a parallel direction to central longitudinal axis 1799. Also in the loaded state, pointed portions 1701-1705 point distally. When in a loaded state, clip 1700 may be configured to extend around body 810. FIG. 18 shows three identical clips 1700, 1801, 1802 stacked together, with pointed portions 1701-1705 aligned and nested together to conserve space when stacked together. In operation, when clip 1700 is pulled by cord 838 off of body 810, clip 1700 may transition from a loaded state shown in FIG. 18 to an equilibrium state shown in FIG. 17.

Figure 20:
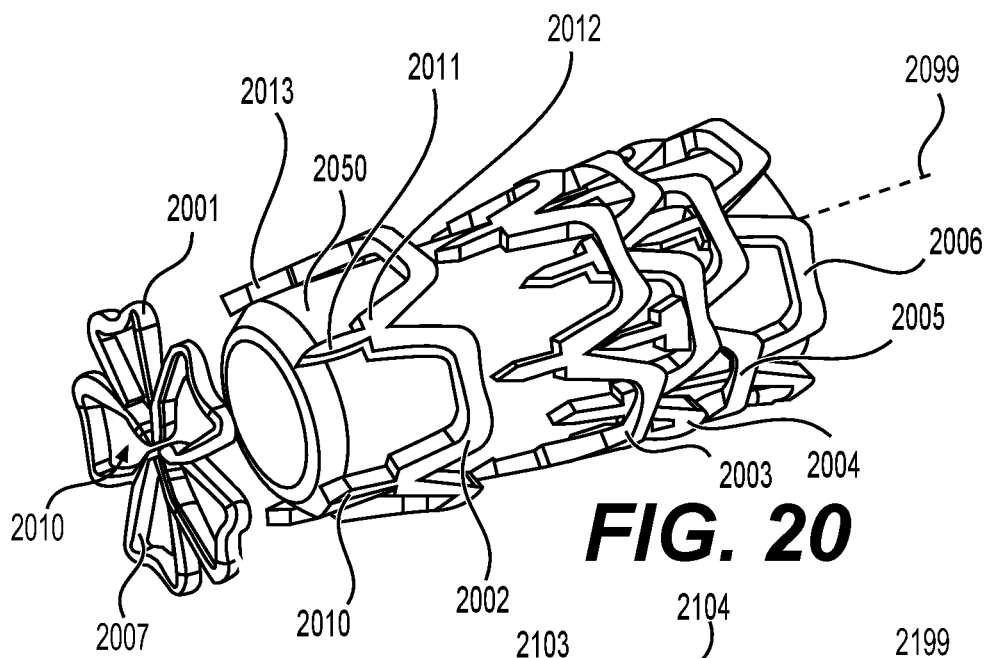
FIG. 20 illustrates a perspective view of exemplary clips and a portion of a body, according to aspects of the disclosure.

FIG. 20 illustrates exemplary clips 2001-2006, with clips 2002-2006 positioned around an exemplary body 2050. Clips 2001-2006 may include any of the above-described features of clip 1700. Clip 2001 is shown in an equilibrium state with surface 2007 facing radially-inward towards central longitudinal axis 2099 of lumen 2010, and clips 2002-2006 are shown in a loaded state. In some examples, pointed portions 2010, 2011, 2013 of clips 2001-2006 may be sharp and configured to cut tissue. Clips 2001-2006 overlap each other on body 2050; and each clip 2001-2006 is rotated about central longitudinal axis 2099 relative to adjacent clips 2001-2006.

Figure 21:
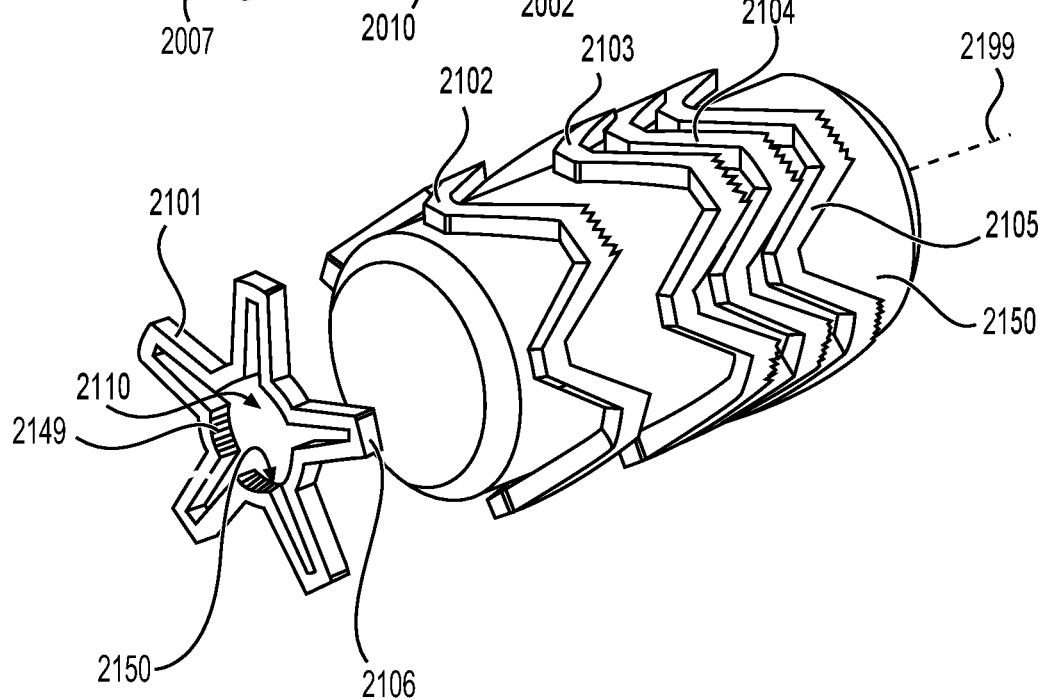
FIG. 21 illustrates a perspective view of exemplary clips and a portion of a body, according to aspects of the disclosure.

FIG. 21 illustrates exemplary clips 2101-2105, with clips 2102-2105 positioned around an exemplary body 2150. Clip 2101 is shown in an equilibrium state, and clips 2102-2105 are shown in loaded states. Each of clips 2101-2105 may include saw-toothed portions 2149, 2150 configured to engage tissue. Saw toothed portions 2149, 2150 may face radially-inward towards central longitudinal axis 2199 of lumen 2110 when clip 2100 is in an equilibrium state. Clip 2100 includes five saw toothed portions 2149, 2150. In other embodiments, any number of saw toothed portions 2149, 2150 may be included in a clip. Clips 2103-2105 are shown nested within each other and positioned over body 2150. Nesting clips 2101-2105 within adjacent clips 2101-2105 when positioned on body 2150 may allow a larger number of clips 2101-2105 to be positioned on body 2150. When clip 2101 transitions from a loaded state, as shown in clips 2102-2105 in FIG. 21, to an equilibrium state, toothed portions 2149, 2150 may move towards central longitudinal axis 2199. When clips 2101-2105 are in an equilibrium state, saw toothed portions 2149, 2150 may be aligned with central longitudinal axis 2199. Saw toothed portions 2149, 2150 may enhance the grip of the clip 2101-2105 onto tissue.

Figure 22:
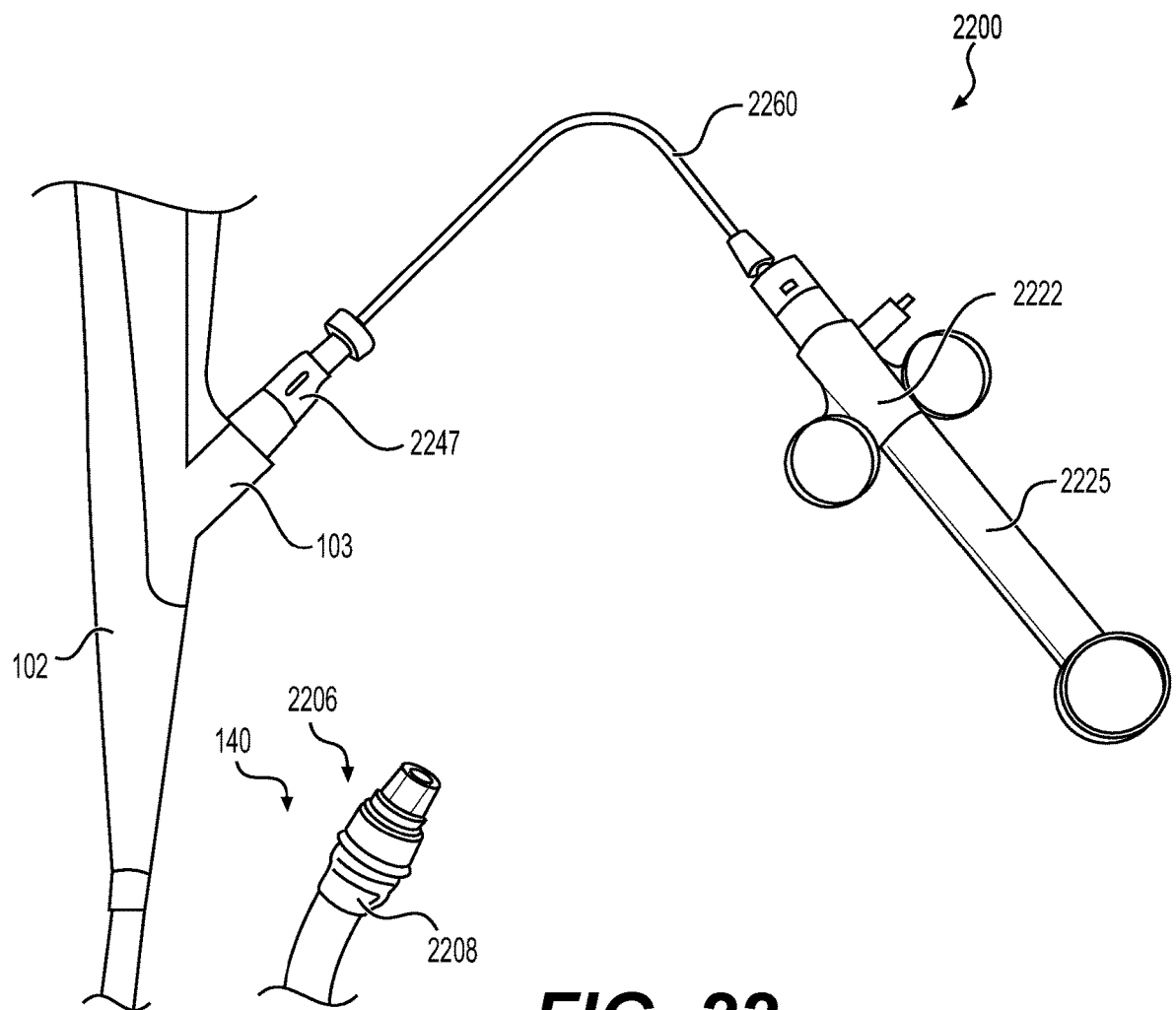
FIG. 22 illustrates a portion of an exemplary medical system, according to aspects of the disclosure.

FIG. 22 illustrates an exemplary handle assembly 2200 and portions of endoscope 101. Handle assembly 2200 may be used with any of the medical devices described in this disclosure and may have any of the features discussed in relation to any of the medical devices described in this disclosure. Handle 225 including actuator 2222 may be coupled to a flexible connector 2260. Flexible connector 2260 may include an adapter 2247 configured to couple to working channel port 103 of endoscope handle 102. Actuator 2222 may translate on a handle 2225. Distal portion 2206 of an exemplary medical device may be coupled to distal portion 140 of endoscope 101 via coupler 2208. Distal portion 2206 may be any of distal portions 206, 606, 806, and actuator 2222 may be used to either open and close a jaws assembly or deploy clips from distal portion 2206. In handle assembly 2200, control wire 216, control wires 616, 617, or tripwire 833 may be positioned within working channel 106 of endoscope 101 and within connector 2260, and ultimately connect to actuator 2222.

Figure 23:
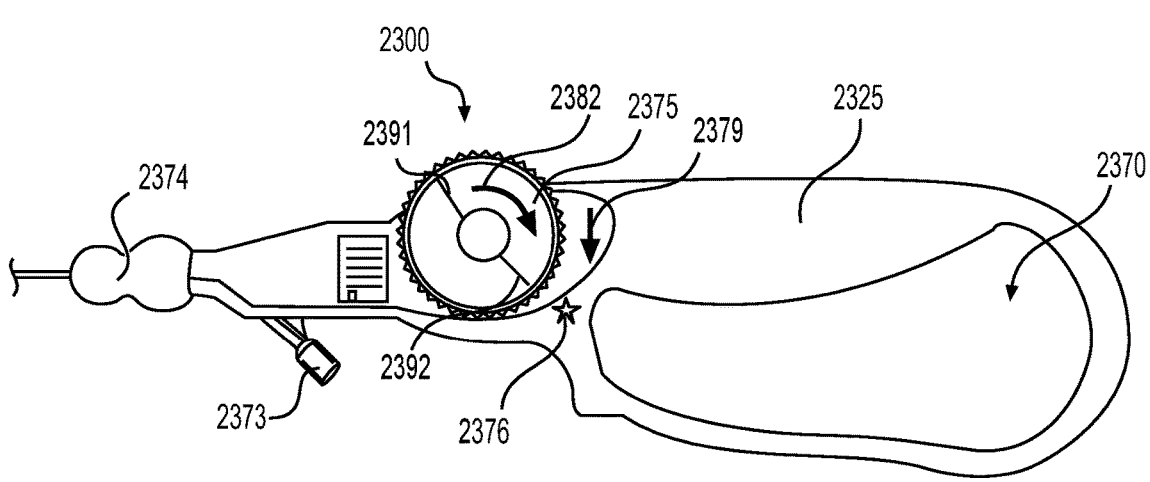
FIG. 23 illustrates components of an exemplary handle assembly, according to aspects of the disclosure.

FIG. 23 illustrates an exemplary handle assembly 2300 for use with medical device 800. Handle assembly 2300 may include handle 2325, handle hub 2374, knob 2375, connector 2373, and an electric plug (not shown). Handle 2325 may include an aperture 2370 configured to receive fingers and/or a hand or a user. Knob 2375 may include two markings 2391, 2392 and an arrow 2382. Arrows 2379, 2382 may indicate the direction a user needs to rotate knob 2375 to deploy or dispense a clip. By utilizing a knob 2375 instead of an actuator similar to actuator 2222, a larger amount of tripwire and/or cord may be used in a medical device and a large amount of clips may be dispensed from the medical device, such as medical device 800. That larger amount of tripwire and/or cord can be spooled around a portion of knob 2375, or other portion of assembly 2300, as knob 2375 is rotated to dispense clips. In some examples, rotating knob 2375 approximately one hundred and eighty degrees will dispense one clip from a medical device. In some examples, when one of markings 2391, 2392 is aligned with the star mark 2376, handle 2325 may generate an audible ratchet or click sound, and knob 2375 may be prevented from rotating in the direction opposite of arrow 2382, which may keep tripwire or cord of the medical device taught. Handle hub 2374 may be rotatable relative to handle 2325, and connector 2373 may provide access to interior portions of the medical device, such as access to tube 807 of medical device 800.

Figure 24:
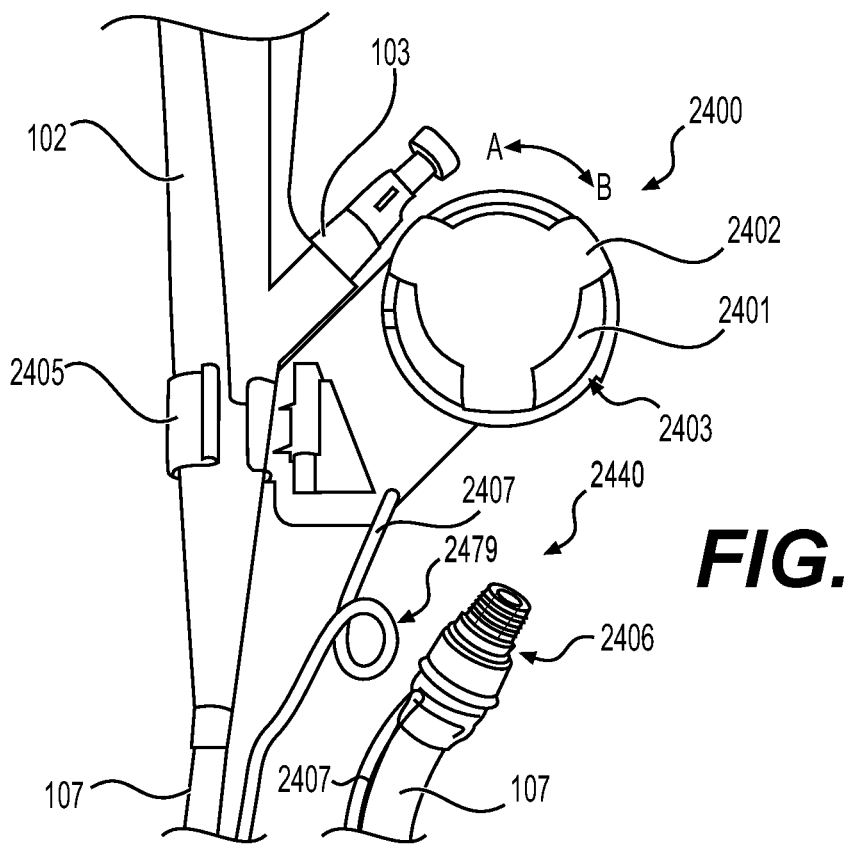
FIG. 24 illustrates portions of an exemplary medical system, according to aspects of the disclosure.

FIG. 24 illustrates an exemplary medical device 2440 with handle assembly 2400. Handle assembly 2400 may be used with any of the medical devices described in this disclosure, such as medical device 800, and medical device 2440 may include any of the features described in this disclosure in connection with medical device 800. Medical device 2440 may include tube 2407 connecting handle assembly 2400 with distal portion 2406, and distal portion 2406 may be coupled to shaft 107 of endoscope 101. Tube 2407 may include a loop 2479 at a proximal portion of tube 2307 to take up excess length of a longer than needed tube 2407. Handle assembly 2400 may be coupled to handle 102 via a bracket 2405, and bracket 2405 may be configured to couple handle assembly 2400 to handle 102 at a portion of handle 102 distal to working channel port 103. A tripwire of medical device 2440 similar to tripwire 833 may extend from distal portion 2406 through tube 2407 to handle body 2401. Tripwire 833 may be coupled to knob 2402, and knob 2402 may be rotatably coupled to handle body 2401. In some examples, when knob 2402 is rotated in the A or B direction approximately one hundred and eighty degrees, a clip is dispensed from distal portion 2406. In other examples, a clip may be dispensed from distal portion 2406 when knob 2402 is rotated any suitable number of degrees in the A or B direction. In some examples, knob 2402 may include a ratchet assembly and may be prevented from rotating in the opposite direction (A or B) from the direction the knob is turned to dispense a clip once a clip is deployed. In other examples, handle assembly 2400 may be coupled to working channel port 103, may receive a tripwire from working channel port, and may not include tube 2407. In some examples, handle assembly 2400 may include a slack knob (not shown) which may be used to tighten a tripwire and take up slack in tripwire.

Figure 25:
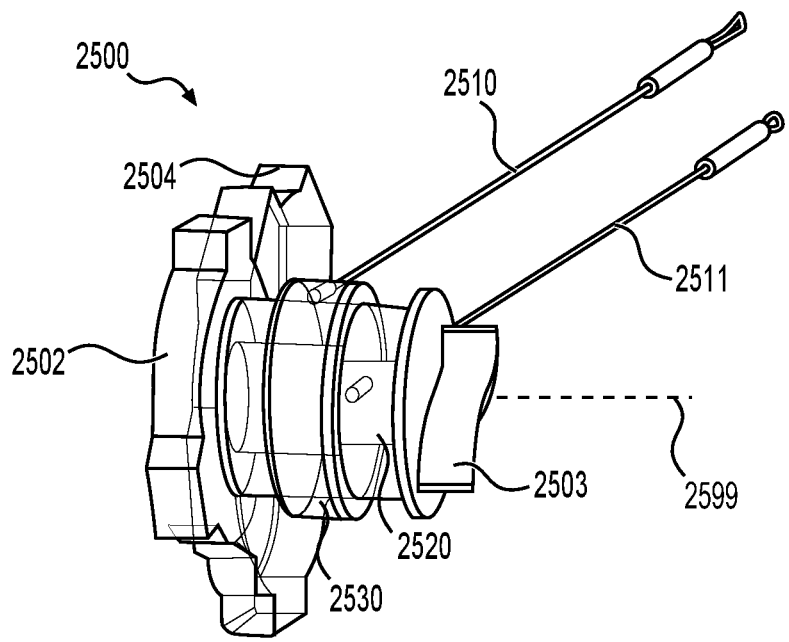
FIG. 25 illustrates components of an exemplary handle assembly, according to aspects of the disclosure.

FIG. 25 illustrates components of an alternative embodiment of a handle assembly that may include any of the above-described features of handle assembly 2400. FIG. 25 will be discussed in further detail below in relation to medical device 2600.

Figure 26:
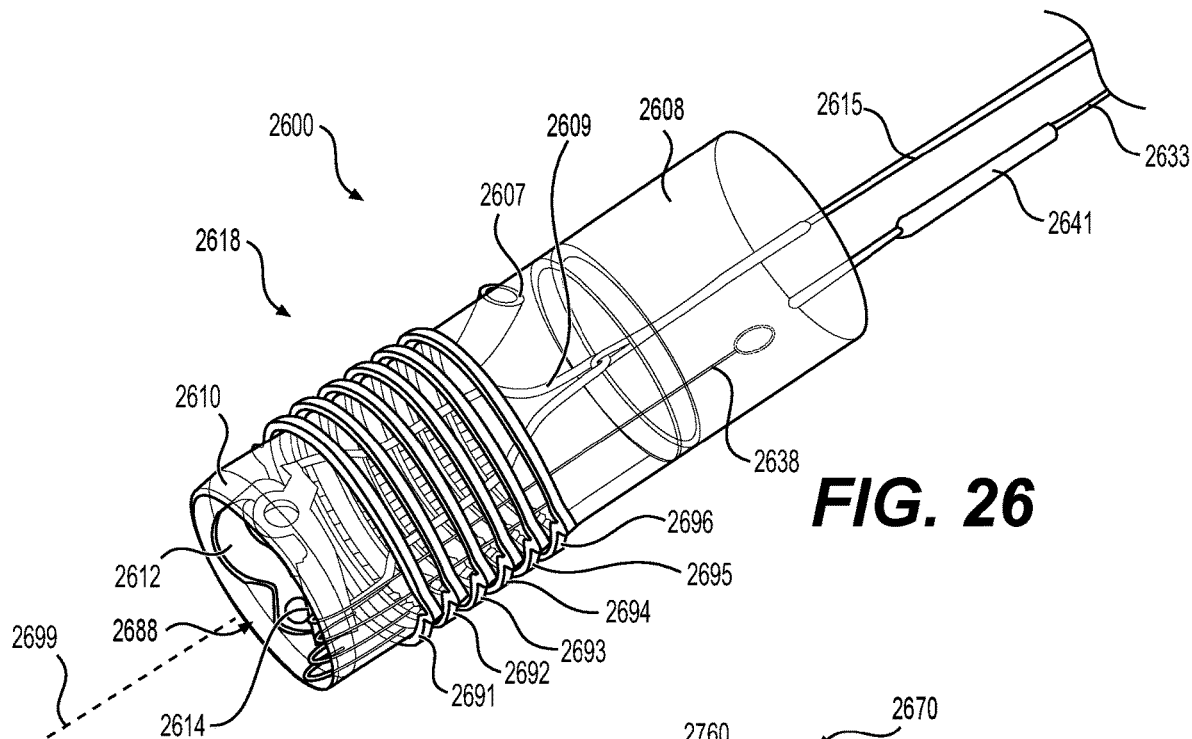
FIG. 26 illustrates a distal portion of an exemplary medical device, according to aspects of the disclosure.
Figure 27:
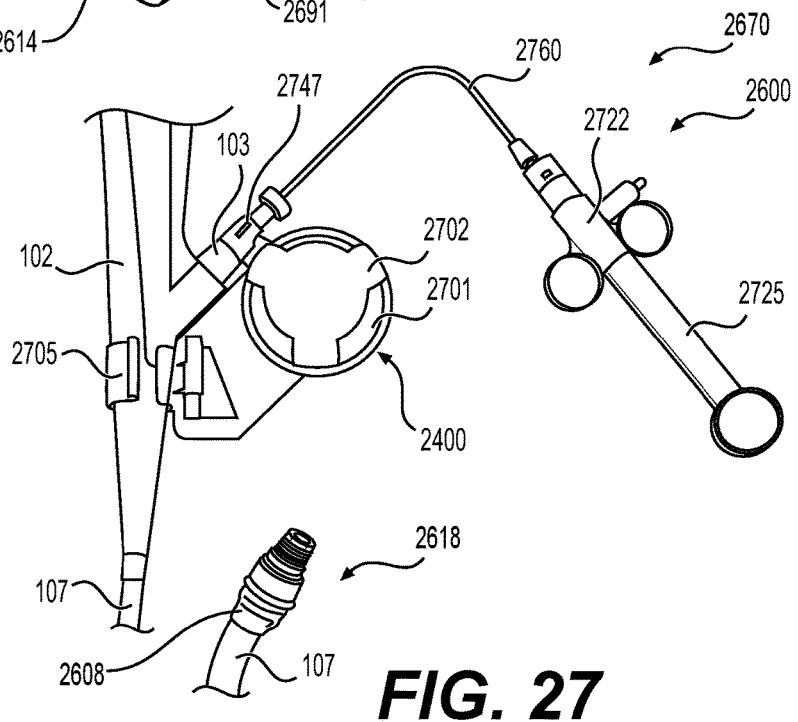
FIG. 27 illustrates portions of an exemplary medical system, according to aspects of the disclosure.

FIG. 26 illustrates a distal portion 2618 of an exemplary medical device 2600, and FIG. 27 illustrates proximal and distal portions of medical device 2600 coupled to endoscope 101. Medical device 2600 may have any of the features described in this disclosure in relation to any of the other medical devices 200, 600, 800. Medical device 2600 may include coupler 2608, body 2610, jaws 2612, 2614, actuation wire 2609, and control wire 2615. Jaws 2612, 2614 may be opened and closed via proximal and distal movement of control wire 2615 in the same manner as jaws 212, 214 in medical device 200. Body 2610 and coupler 2608 may include a central lumen 2688 extending longitudinally through body 2610 and coupler 2608, and lumen 2688 may be configured to receive tissue. A tube port 2607 may be on body 2610 and may be configured to couple to a tube to provide access to the interior of body 2610. In other examples, body 2610 may not include tube port 2607. Medical device 2600 may also include clips 2691-2696 positioned around body 2610. A tripwire 2633 is shown disconnected from a cord 2638 for illustration purposes only, and tripwire 2633 would be coupled to cord 2638, via a lock sleeve 2641, during operation of medical device 2600, as in prior described embodiments. Tripwire 2633 and control wire 2615 may be color-coded, lock sleeves on each of tripwire 2633 and control wire 2614 may be color coded, and/or one of tripwire 2633 and control wire 2615 may be longer than the other to allow a user to distinguish between tripwire 2633 and control wire 2615. Clips 2691-2696 would be dispensed or deployed from medical device 2600 in the same manner as described herein in relation to medical device 800. Cord 2638 of medical device 2600 is positioned radially-outer from jaws 2612, 2614 relative to central longitudinal axis 2699 of medical device 2600, which may prevent cord 2638 from being cut by jaws 2612, 2614 during operation. In some examples, both tripwire 2633 and control wire 2615 may be positioned within working channel 106 of endoscope 101 during use of medical device 2600. In other examples, one or both of tripwire 2633 and control wire 2615 may be positioned within a tube extending from side tube port 2607 during use of medical device 2600, and the tube would extend outside of endoscope 101.

FIG. 27 illustrates proximal and distal portions of medical device 2600 coupled to endoscope 101. Handle assembly 2670 of medical device 2600 may include a handle 2725 and a knob assembly 2400. Handle assembly 2670 may include any of the features discussed in this disclosure related to other medical devices and other handle assemblies, such as handles 202, 602, 802 and handle assembly 2200, 2300, 2400. Distal portion 2618 may be coupled to distal portion 108 of endoscope 101 with coupler 2608 positioned around shaft 107. In handle assembly 2670, actuator 2722 may be connected to control wire 2615 and may be configured to open and close jaws 2612, 2614 via proximal and distal movement of actuator 2722 relative to handle 2725. Control wire 2615 may be positioned within working channel 106 of endoscope 101, and may extend through connector 2760 to be coupled to actuator 2722 within handle 2725. Tripwire 2633 may also extend from distal portion 2618 through working channel 106 and out of working channel port 103 into knob assembly 2400. Knob assembly 2400 may control deployment of clips 2691-2696, and rotation of knob 2702 relative to body 2701 may deploy one or more clips 2691-2696. Bracket 2705 may couple knob assembly 2400 to handle 102 such that tripwire 2633 may extend into knob assembly 2400 while allowing space for control wire 2615 to be positioned in connector 2760 and working channel port 103. In some examples, adapter 2747 may connect working channel port 103 with both connector 2760 and knob assembly 2400, such that tripwire 2633 may extend through adapter 2747 into knob assembly 2400, and control wire 2615 may extend through adapter 2747 into connector 2760.

FIG. 25 illustrates components of an alternative embodiment of a handle assembly 2500 that includes three knobs 2502, 2503, 2504, and may be referred to herein as a dual-reel handle assembly. The body of this dual-reel handle assembly is removed for illustration purposes. Any of the features discussed in this disclosure may be incorporated into a dual-reel handle assembly using the components shown in FIG. 25. Dual reel handle assembly 2500 may be configured for use with distal portion 2618 of medical device 2600. A first knob 2502 may be coupled to a tripwire 2511 via an axle 2520, and tripwire 2511 may correspond to tripwire 2633 of medical device 2600. A second knob 2504 may be coupled to a control wire 2510 via an axle 2530, and control wire 2510 may correspond to control wire 2615 of medical device 2600. Axle 2520 is positioned through an aperture in axle 2530 and an aperture in 2504, to connect axle 2520 to 2502. Axle 2520 rotates within 2530. Axle 2530 rotates over axle 2520. Tripwire 2511 and control wire 2510 may be positioned within working channel 106 of endoscope 101 during operation, and dual-reel handle assembly 2500 may receive tripwire 2511 and control wire 2510 from working channel port 103. Alternatively tripwire 2511 and control wire 2510 may be positioned within a tube positioned outside of endoscope 101, similar to tube 2407 shown in FIG. 24, during operation, and dual-reel handle assembly may receive tripwire 2511 and control wire 2510 from the tube. A third knob 2503 may be also coupled to tripwire 2511, via a fixed connection between knob 2503 and axle 2520. Knob 2503 may be configured to adjust the slack in tripwire 2511 prior to and during operation of the medical device. In some examples, first knob 2502 may be ratcheted and may be limited to rotation in only one direction. A user may rotate first knob 2502 to deploy one or more clips 2691-2696 from the medical device. The user may also rotate second knob 2504 to move control wire 2510 proximally or distally to open or close jaws 2612, 2614. By providing a dual-reel handle assembly including components of FIG. 25, a user may not require help from additional users during operation of the medical device, because a user's first hand may hold handle 102 of endoscope 101 and the user's second hand may actuate knobs 2502-2504 of the dual-reel handle assembly to operate medical device 2600.

In other examples, a similar knob assembly as shown in FIG. 25 may be utilized in a handle assembly similar to handle assembly 2300.

To use medical device 2600, a user may first couple coupler 2608 to distal portion 108 of endoscope 101. In some examples, the user may first position control wire 2615 and tripwire 2633 within working channel 106, and then couple control wire 2615 to actuation wire 2609 and couple tripwire 2633 to cord 2638. In some examples, the user may feed each of control wire 2615 and tripwire 2633 from a proximal end of endoscope 101 through working channel port 103 and through working channel 106 to distal portion 108, and then couple control wire 2615 to actuation wire 2609 and couple tripwire 2633 to cord 2638. The user may then adjust the length of tripwire 2633 and/or control wire 2615, such as via third knob 2503, to tighten each wire and take up any slack in the wires. In other examples, a user may couple coupler 2608 to distal portion 108, and tripwire 2633 and control wire 2615 may already be positioned within a tube separate from endoscope 101.

The user may then insert endoscope 101 and medical device 2600 into a body of a patient, and position the devices proximate to a target area within the body. The user may then apply suction to working channel 106 or another channel within endoscope 101 to pull tissue into lumen 2688. The user may then grasp or cut tissue by closing jaws 2612, 2614 via moving control wire 2615 proximally. In some examples, the user may move actuator 2722 of handle assembly 2670 proximally to close jaws 2612, 2614, and in other examples the user may rotate second knob 2504 of dual reel handle assembly 2500 discussed in relation to FIG. 25. The user may then deploy one or more clips 2691-2696 by moving tripwire 2633 proximally. In some examples, the user may rotate knob 2702 of handle assembly 2670 to deploy one or more clips 2691-2696. In other examples, the user may rotate first knob 2502 of dual reel handle assembly 2500 discussed in relation to FIG. 25 to deploy one or more clips 2691-2696. The user may repeat the steps of opening and closing jaws and deploying clips 2691-2696 multiple times during a single procedure. The user may then remove endoscope 101 and medical device 2600 from the body of the patient.

It also should be understood that one or more aspects of any of the medical devices, systems, and methods described herein may be used for cutting, dissecting, treating, or ablating tissue in any part of the human body. For example, any of the medical devices described herein may be used in medical procedures such as for Endoscopic Submucosal Dissection (ESD), cancer treatment, kidney or bladder biopsies or resections, and/or other procedures where removal, clipping, dissection, fulguration, and/or ablation of the type of tissue is needed. Any of the clips 891-896, 1191, 1200, 1400, 1600, 1700, 2001, 2101, 2691-2696 discussed in this disclosure may be used as marker bands, radiopaque marker bands, or elastic bands.

Various aspects discussed herein may help reduce procedure time, increase tissue treatment effectiveness, reduce the risks to the subject, etc.

Although the exemplary embodiments described above have been disclosed in connection with medical devices for manipulating and resecting human tissue through the working channel of a medical device, a natural orifice, or by incision, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of the this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the this disclosure as defined by the following claims.

We claim:

1. A medical device adapted for use with a delivery device, the medical device comprising:
    a handle including a first actuator and a second actuator;
    a body adapted to releasably mount to a distal portion of the delivery device;
    at least one clip positioned around an exterior surface of the body;
    a cord coupled to each of the at least one clip, wherein the cord includes a loop;
    a tripwire, wherein the tripwire includes a hook, wherein the hook of the tripwire is positioned through the loop of the cord, and wherein the tripwire is releasably coupled to the at least one clip;
    wherein the tripwire extends from the body to the handle, wherein actuation of the second actuator is configured to deploy the at least one clip from the body;
    a pair of jaws rotatably coupled to the body, wherein the tripwire is positioned radially outward from the pair of jaws relative to a central longitudinal axis of the body; and
    a Y-shaped control wire including a proximal end, a first distal end, and a second distal end, wherein the proximal end is coupled to the first actuator, wherein the first distal end is coupled to one jaw of the pair of jaws, wherein the second distal end is coupled to the other jaw of the pair of jaws, and wherein the control wire includes Z-shaped bends adjacent to the couplings of the first distal end and the second distal end of the control wire to the respective jaws; and
    wherein the first actuator is configured to open and close the pair of jaws;
    wherein the tripwire and the control wire are positioned within a tube extending outside of the delivery device, and wherein the tube is coupled to the handle.

2. The medical device of claim 1, wherein the handle is configured to mount to a handle of the delivery device, and the delivery device is an endoscope.

3. The medical device of claim 2, wherein the control wire is configured to be positioned within a working channel of the endoscope.

4. The medical device of claim 2, wherein the control wire is configured to be coupled to a source of electrical energy to transmit electrical energy to the pair of jaws.

5. The medical device of claim 1, wherein the control wire includes a first control wire and an actuation wire coupled to the first control wire, wherein the actuation wire includes a ring portion, wherein the ring portion is configured to receive a distal loop of the first control wire.

6. The medical device of claim 1, wherein proximal movement of the first actuator moves the control wire proximally and closes the pair of jaws.

7. The medical device of claim 1, wherein the handle includes (1) a handle body on which the first actuator translates, and (2) a connector configured to couple to a port of the delivery device.

8. The medical device of claim 1, wherein the handle includes:
    a first body, wherein the first actuator is moveably coupled to the first body; and
    a second body comprising a bracket configured to couple to a handle of the delivery device, wherein the second actuator is a knob rotatably coupled to the second body.

9. The medical device of claim 1, wherein the handle includes:
    a first body including a bracket configured to couple to a handle of the delivery device;
    wherein the first actuator is a first knob rotatably coupled to the first body; and
    wherein the second actuator is a second knob rotatably coupled to the first body.

10. The medical device of claim 1, wherein one of the at least one clip includes at least one of:
    a first clip including a first side coupled to a second side via two square pegs, wherein each of the first side and the second side includes shape memory material;
    a second clip including a first side and a second side, wherein the first side includes a first contoured edge portion including a sharp edge, and the second side includes a second contoured edge portion including a sharp edge, wherein the first contoured edge portion is complimentary to the second contoured edge portion;
    a third clip including a plurality of pointed portions pointed towards a center of a central lumen of the third clip when the third clip is in an equilibrium state, wherein the plurality of pointed portions are pointed in a distal direction when the third clip is in a loaded state on the body; and
    a fourth clip including a plurality of saw-toothed portions facing towards a center of a central lumen of the fourth clip when the fourth clip is in an equilibrium state, wherein the plurality of saw-toothed portions are pointed in a distal direction when the fourth clip is in a loaded state on the body.

11. The medical device of claim 1, wherein the body includes a first guide clip and a second guide clip positioned on an inner wall of the body, wherein the actuation wire extends through the first guide clip and the second guide clip.

12. A medical device adapted for use with a delivery device, the medical device comprising:
- a body adapted to releasably mount to a distal portion of the delivery device;
- a pair of jaws rotatably coupled to the body;
- at least one clip positioned around an exterior surface of the body;
- a cord, wherein the cord is coupled to each of the at least one clip, wherein the cord includes a loop; and
- a tripwire, wherein the tripwire includes a hook, wherein the hook of the tripwire is positioned through the loop of the cord, wherein the tripwire is positioned radially outward from the pair of jaws relative to a central longitudinal axis of the body, and wherein the tripwire is releasably coupled to the at least one clip and extends proximally from the body; and
- a Y-shaped control wire including a proximal end, a first distal end, and a second distal end, wherein the first distal end is coupled to one jaw of the pair of jaws, wherein the first distal end is coupled to one jaw of the pair of jaws, wherein the second distal end is coupled to the other jaw of the pair of jaws, and wherein the control wire includes Z-shaped bends adjacent to the couplings of the first distal end and the second distal end of the respective jaws;
- wherein the tripwire and the control wire are positioned within a tube extending outside of the delivery device, and wherein the tube is coupled to a handle;
- wherein translation of the control wire is configured to open and close the pair of jaws; and
- wherein proximal movement of the tripwire is configured to dispense the at least one clip from the body.

13. The medical device of claim 12, wherein the body includes a coupler portion configured to mate with the distal portion of the delivery device.

14. A medical device adapted for use with a delivery device, the medical device comprising:
- a body adapted to mount to a distal portion of the delivery device;
- a pair of jaws rotatably coupled to the body and the body is coupled to a barrel;
- a Y-shaped control wire including a proximal end, a first distal end, and a second distal end, wherein the first distal end is coupled to one jaw of the pair of jaws, wherein the second distal end is coupled to the other jaw of the pair of jaws, and wherein the control wire includes Z-shaped bends adjacent to the couplings of the first distal end and the second distal end of the respective jaws;
- at least one clip positioned around an exterior surface of the body;
- a cord, wherein the cord is coupled to each of the at least one clip, wherein the cord includes a loop;
- a tripwire positioned radially outward from the pair of jaws relative a central longitudinal axis of the body, wherein the tripwire includes a hook, wherein the hook of the tripwire is positioned through the loop of the cord and the tripwire is releasably coupled to the at least one clip;
- a handle including a first knob and a second knob, wherein the handle is adapted to mount to a handle of the delivery device; and
- a tube, wherein the tube extends outside of the delivery device, and wherein the tube is coupled to the handle of the delivery device;
- wherein actuation of the first knob is configured to open and close the pair of jaws;
- wherein rotation of the second knob is configured to dispense the at least one clip from the barrel; and
- wherein the tripwire and the control wire are positioned within the tube.

15. The medical device of claim 14, wherein the handle further includes a third knob, wherein the third knob is configured to move the tripwire to tighten or loosen the tripwire.

* * * * *